United States Patent
Edidin et al.

(10) Patent No.: US 8,409,257 B2
(45) Date of Patent: Apr. 2, 2013

(54) SYSTEMS AND METHODS FOR FACET JOINT STABILIZATION

(75) Inventors: Avram Allan Edidin, Portola Valley, CA (US); Nikolas F. Kerr, Germantown, TN (US); Greg C. Marik, Collierville, TN (US); Newton H. Metcalf, Jr., Memphis, TN (US); Tanmay Mishra, Mountain View, CA (US); Michael A. Smith, San Jose, CA (US); Jusong Xia, Collierville, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 146 days.

(21) Appl. No.: 12/943,606

(22) Filed: Nov. 10, 2010

(65) Prior Publication Data

US 2012/0116454 A1 May 10, 2012

(51) Int. Cl.
*A61B 17/70* (2006.01)
*A61B 17/88* (2006.01)

(52) U.S. Cl. ........ 606/279; 606/247

(58) Field of Classification Search .......... 606/246–247, 606/279, 86 A, 98–99, 107, 79–80, 105; *A61B 17/70, 17/88*
See application file for complete search history.

(56) References Cited

U.S. PATENT DOCUMENTS

| | | | |
|---|---|---|---|
| 2,631,584 A | 3/1953 | Purificato | |
| 2,760,488 A | 8/1956 | Pierce | |
| 4,175,555 A | 11/1979 | Herbert | |
| 4,341,206 A | 7/1982 | Perrett et al. | |
| 4,501,269 A | 2/1985 | Bagby | |
| 4,640,271 A | 2/1987 | Lower | |
| 4,710,075 A | 12/1987 | Davison | |
| 4,858,601 A | 8/1989 | Glisson | |
| 4,988,351 A | 1/1991 | Paulos et al. | |
| 5,026,373 A | 6/1991 | Ray et al. | |

(Continued)

FOREIGN PATENT DOCUMENTS

| | | |
|---|---|---|
| WO | WO 00/53126 | 9/2000 |
| WO | WO 02/34120 A2 | 5/2002 |

(Continued)

OTHER PUBLICATIONS

Boucher, "A Method of Spinal Fusion", Dept. of Orthopedic Surgery, Shaughnessy Hospital, Dept. of Veterans Affairs of Canada, Vancouver, B.C. and Dept. of Orthopedic Surgery, University of British Columbia, The Journal of Bone and Joint Surgery, vol. 41 B, No. 2, May 1959, pp. 248-259.

(Continued)

*Primary Examiner* — Ellen C Hammond
*Assistant Examiner* — Jacqueline Johanas

(57) ABSTRACT

In one form, a method for stabilization of a facet joint of the spinal column includes forming a cavity between adjacent bones defining the facet joint and positioning an implant in the cavity between the adjacent bones. In one aspect of this form, the method also includes positioning a bone anchor across the facet joint and engaging the bone anchor with each of the adjacent bones to force the bones toward one another and clamp the implant therebetween. In a further aspect of this form, the implant is a cancellous bone dowel and becomes fractured into a plurality of fragments upon being clamped between the adjacent bones and/or otherwise interacting with the bone anchor. In another form, systems and devices for performing percutaneous facet joint stabilization and/or fusion are provided. However, different forms and applications are also envisioned.

21 Claims, 24 Drawing Sheets

U.S. PATENT DOCUMENTS

| | | |
|---|---|---|
| 5,180,388 A | 1/1993 | DiCarlo |
| 5,217,462 A | 6/1993 | Asnis et al. |
| 5,368,593 A | 11/1994 | Stark |
| 5,382,250 A | 1/1995 | Kraus |
| 5,409,493 A | 4/1995 | Greenberg |
| 5,484,437 A | 1/1996 | Michelson |
| 5,527,312 A | 6/1996 | Ray |
| 5,536,127 A | 7/1996 | Pennig |
| D374,283 S | 10/1996 | Michelson |
| 5,571,191 A | 11/1996 | Fitz |
| 5,591,207 A | 1/1997 | Coleman |
| 5,607,428 A | 3/1997 | Lin |
| 5,690,633 A | 11/1997 | Taylor et al. |
| 5,725,529 A | 3/1998 | Nicholson et al. |
| 5,741,253 A | 4/1998 | Michelson |
| 5,741,261 A | 4/1998 | Moskovitz et al. |
| 5,772,661 A | 6/1998 | Michelson |
| 5,797,909 A | 8/1998 | Michelson |
| 5,810,828 A | 9/1998 | Lightman et al. |
| 5,860,973 A | 1/1999 | Michelson |
| 5,890,897 A | 4/1999 | Kruger et al. |
| 5,895,389 A | 4/1999 | Schenk et al. |
| 5,899,904 A | 5/1999 | Errico et al. |
| 5,899,905 A | 5/1999 | Errico et al. |
| 5,904,685 A | 5/1999 | Walawalkar |
| 5,925,047 A | 7/1999 | Errico et al. |
| 5,954,635 A | 9/1999 | Foley et al. |
| 5,954,722 A | 9/1999 | Bono |
| 5,989,255 A | 11/1999 | Pepper et al. |
| 6,080,155 A | 6/2000 | Michelson |
| 6,083,225 A | 7/2000 | Winslow et al. |
| 6,096,038 A | 8/2000 | Michelson |
| 6,110,178 A | 8/2000 | Zech et al. |
| 6,123,711 A | 9/2000 | Winters |
| 6,200,322 B1 | 3/2001 | Branch et al. |
| 6,206,885 B1 | 3/2001 | Ghahremani et al. |
| 6,210,412 B1 | 4/2001 | Michelson |
| 6,217,509 B1 | 4/2001 | Foley et al. |
| 6,224,595 B1 | 5/2001 | Michelson |
| 6,274,498 B1 | 8/2001 | Moore et al. |
| 6,287,313 B1 | 9/2001 | Sasso |
| 6,302,887 B1 | 10/2001 | Spranza et al. |
| 6,306,140 B1 | 10/2001 | Siddiqui |
| 6,306,142 B1 | 10/2001 | Johanson et al. |
| 6,319,254 B1 | 11/2001 | Giet et al. |
| 6,436,098 B1 | 8/2002 | Michelson |
| 6,485,518 B1 | 11/2002 | Cornwall et al. |
| 6,494,883 B1 * | 12/2002 | Ferree ............... 606/247 |
| 6,524,316 B1 | 2/2003 | Nicholson et al. |
| 6,540,747 B1 | 4/2003 | Marino |
| 6,547,795 B2 | 4/2003 | Schneiderman |
| 6,562,046 B2 | 5/2003 | Sasso |
| 6,575,974 B2 | 6/2003 | Gotfried |
| 6,648,893 B2 | 11/2003 | Dudasik |
| 6,660,007 B2 | 12/2003 | Khanna |
| 6,669,698 B1 | 12/2003 | Tromanhauser et al. |
| 6,695,851 B2 | 2/2004 | Zdeblick et al. |
| 6,723,095 B2 | 4/2004 | Hammerslag |
| 6,849,064 B2 | 2/2005 | Hamada |
| 6,951,562 B2 | 10/2005 | Zwirnmann |
| 6,966,930 B2 | 11/2005 | Arnin et al. |
| 6,980,849 B2 | 12/2005 | Sasso |
| 7,048,477 B2 | 5/2006 | Abrams |
| 7,060,068 B2 | 6/2006 | Tromanhauser et al. |
| 7,175,625 B2 | 2/2007 | Culbert |
| 7,211,085 B2 | 5/2007 | Michelson |
| 7,223,269 B2 | 5/2007 | Chappuis |
| 7,354,442 B2 | 4/2008 | Sasso et al. |
| 7,396,360 B2 | 7/2008 | Lieberman |
| 7,491,203 B2 | 2/2009 | Harris, Jr. et al. |
| 7,503,993 B2 | 3/2009 | Okuyama et al. |
| 7,569,054 B2 | 8/2009 | Michelson |
| 7,699,878 B2 | 4/2010 | Pavlov et al. |
| 7,708,761 B2 | 5/2010 | Petersen |
| 7,824,429 B2 | 11/2010 | Culbert et al. |
| 7,837,713 B2 | 11/2010 | Petersen |
| 7,901,439 B2 | 3/2011 | Horton |
| 8,021,392 B2 * | 9/2011 | Petersen ............... 606/247 |
| 8,070,782 B2 * | 12/2011 | McKay ............... 606/279 |
| 2002/0151895 A1 | 10/2002 | Soboleski et al. |
| 2002/0169471 A1 | 11/2002 | Ferdinand |
| 2003/0032960 A1 | 2/2003 | Dudasik |
| 2003/0125738 A1 | 7/2003 | Khanna |
| 2003/0125749 A1 | 7/2003 | Yuan et al. |
| 2003/0208202 A1 | 11/2003 | Falahee |
| 2004/0087948 A1 | 5/2004 | Suddaby |
| 2004/0093001 A1 | 5/2004 | Hamada |
| 2004/0111093 A1 | 6/2004 | Chappuis |
| 2004/0127989 A1 | 7/2004 | Dooris et al. |
| 2004/0143268 A1 | 7/2004 | Falahee |
| 2004/0225292 A1 | 11/2004 | Sasso et al. |
| 2004/0225360 A1 | 11/2004 | Malone |
| 2004/0254575 A1 | 12/2004 | Obenchain et al. |
| 2005/0049705 A1 * | 3/2005 | Hale et al. ............... 623/17.11 |
| 2005/0090833 A1 | 4/2005 | DiPoto |
| 2005/0101985 A1 | 5/2005 | Hamada |
| 2005/0124993 A1 | 6/2005 | Chappuis |
| 2005/0149030 A1 | 7/2005 | Serhan et al. |
| 2005/0177240 A1 | 8/2005 | Blain |
| 2005/0197700 A1 | 9/2005 | Boehm, Jr. et al. |
| 2005/0216026 A1 | 9/2005 | Culbert |
| 2005/0240209 A1 | 10/2005 | Hamada |
| 2005/0267480 A1 | 12/2005 | Suddaby |
| 2006/0004367 A1 | 1/2006 | Alamin et al. |
| 2006/0030872 A1 | 2/2006 | Culbert et al. |
| 2006/0064099 A1 | 3/2006 | Pavlov et al. |
| 2006/0079908 A1 | 4/2006 | Lieberman |
| 2006/0084977 A1 * | 4/2006 | Lieberman ............... 606/60 |
| 2006/0085010 A1 | 4/2006 | Lieberman |
| 2006/0085068 A1 | 4/2006 | Barry |
| 2006/0111714 A1 | 5/2006 | Foley |
| 2006/0111779 A1 | 5/2006 | Petersen |
| 2006/0111782 A1 * | 5/2006 | Petersen ............... 623/17.11 |
| 2006/0167487 A1 | 7/2006 | Hamada |
| 2006/0178693 A1 | 8/2006 | Hamada |
| 2006/0264953 A1 | 11/2006 | Falahee |
| 2006/0264954 A1 | 11/2006 | Sweeney, II et al. |
| 2006/0271096 A1 | 11/2006 | Hamada |
| 2006/0276790 A1 | 12/2006 | Dawson et al. |
| 2007/0038216 A1 | 2/2007 | Hamada |
| 2007/0083265 A1 | 4/2007 | Malone |
| 2007/0093841 A1 | 4/2007 | Hoogland |
| 2007/0112428 A1 | 5/2007 | Lancial |
| 2008/0021480 A1 | 1/2008 | Chin et al. |
| 2008/0147079 A1 | 6/2008 | Chin et al. |
| 2008/0154374 A1 * | 6/2008 | Labrom ............... 623/17.12 |
| 2008/0161810 A1 | 7/2008 | Melkent |
| 2008/0234758 A1 | 9/2008 | Fisher et al. |
| 2008/0255618 A1 | 10/2008 | Fisher et al. |
| 2008/0255619 A1 | 10/2008 | Schneiderman et al. |
| 2008/0255622 A1 | 10/2008 | Mickiewicz et al. |
| 2008/0255667 A1 | 10/2008 | Horton |
| 2008/0262555 A1 | 10/2008 | Assell et al. |
| 2008/0306537 A1 | 12/2008 | Culbert |
| 2009/0024166 A1 * | 1/2009 | Carl et al. ............... 606/247 |
| 2009/0036927 A1 | 2/2009 | Vestgaarden |
| 2009/0036986 A1 * | 2/2009 | Lancial et al. ............... 623/17.11 |
| 2009/0054903 A1 | 2/2009 | Falahee et al. |
| 2009/0076551 A1 | 3/2009 | Petersen |
| 2009/0093851 A1 | 4/2009 | Osman |
| 2009/0099602 A1 | 4/2009 | Aflatoon |
| 2009/0125066 A1 * | 5/2009 | Kraus et al. ............... 606/279 |
| 2009/0131947 A1 * | 5/2009 | Aeschlimann et al. ......... 606/93 |
| 2009/0131986 A1 * | 5/2009 | Lee et al. ............... 606/247 |
| 2009/0138053 A1 * | 5/2009 | Assell et al. ............... 606/301 |
| 2009/0157119 A1 * | 6/2009 | Hale ............... 606/247 |
| 2009/0234397 A1 * | 9/2009 | Petersen ............... 606/86 R |
| 2009/0264928 A1 * | 10/2009 | Blain ............... 606/247 |
| 2009/0306571 A1 * | 12/2009 | McCormack et al. ......... 606/90 |
| 2009/0312763 A1 * | 12/2009 | McCormack et al. ......... 606/83 |
| 2009/0312798 A1 * | 12/2009 | Varela ............... 606/247 |
| 2010/0114175 A1 | 5/2010 | McKay |
| 2010/0137910 A1 * | 6/2010 | Cawley et al. ............... 606/247 |
| 2010/0191286 A1 * | 7/2010 | Butler ............... 606/247 |
| 2010/0331883 A1 * | 12/2010 | Schmitz et al. ............... 606/249 |
| 2011/0009872 A1 * | 1/2011 | Mistry et al. ............... 606/99 |

| | | | |
|---|---|---|---|
| 2011/0060366 A1* | 3/2011 | Heim et al. | 606/247 |
| 2011/0077685 A1* | 3/2011 | Carls et al. | 606/247 |
| 2012/0046695 A9* | 2/2012 | Blain | 606/247 |

FOREIGN PATENT DOCUMENTS

| | | |
|---|---|---|
| WO | WO 02/065954 A1 | 8/2002 |
| WO | WO 02/085181 A2 | 10/2002 |
| WO | WO 2004/019757 A2 | 3/2004 |
| WO | WO 2004/037070 A2 | 5/2004 |
| WO | WO 2004/043278 A1 | 5/2004 |
| WO | WO 2005/097005 A1 | 10/2005 |
| WO | WO 2006/045007 A3 | 4/2006 |
| WO | WO 2006/057943 A2 | 6/2006 |
| WO | WO 2006/130791 A2 | 12/2006 |
| WO | WO 2007/002405 A2 | 1/2007 |

OTHER PUBLICATIONS

Foley et al., 28(15S) Spine S26-S35 (2003), "Minimally Invasive Lumbar Fusion," Foley et al., 28(15S) Spine S26-S35 (2003).

Ray, "Posterior Lumbar Interbody Fusions by Implanted Threaded Titanium Cages," Spine Care vol. 2, Chp. 88 (White AH, Schoffermann JA eds.) (1995) 1223-1232.

Chin et al., "Early Results of the Triage Medical® Percutaneous Transfacet Pedicular BONE-LOK® Device for Lumbar Fusion", (2006), 9 pages.

Ray, "Transfacet Decompression with Dowel Fixation: a New Technique for Lumbar Lateral Spinal Stenosis," 43 Acta Neurochir. Suppl. 48-54 (1988) (Ray).

* cited by examiner

SYSTEMS AND METHODS FOR FACET JOINT STABILIZATION

BACKGROUND

The present application relates to systems and methods for performing surgery in a patient, and more particularly but not exclusively relates to systems, devices and techniques for facet joint stabilization and/or fusion.

The human spine serves many functions. The vertebral members of the spinal column protect the spinal cord. The spinal column also supports other portions of the human body. Additionally, moveable facet joints and resilient discs disposed between the vertebral members permit motion between individual vertebral members. Each vertebra includes an anterior body and a posterior arch. The posterior arch includes two pedicles and two laminae that join together to form the spinous process. A transverse process is laterally positioned at the transition from the pedicles to the laminae. Both the spinous process and transverse process provide for attachment of fibrous tissue including, for example, muscle. Two inferior articular processes extend downward from the junction of the laminae and the transverse process. Further, two superior articular processes extend upward from the junction. The articular processes of adjacent vertebrae form the facet joints. The inferior articular process of one vertebra articulates with the superior articular process of the adjacent vertebra. The facet joints may be considered to constitute gliding joints because the articular surfaces glide over one another.

Vertebral implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. Spinal fusion often involves the removal of at least a portion of the vertebral disc and insertion of an interbody implant to create a fused junction between a pair of vertebral bodies. These techniques may also involve the implantation of stabilization members such as, for example, rods or plates, outside of the disc space. In addition to or in lieu of fusion of the adjacent vertebrae across the disc space, the facet joints may be stabilized and/or fused to alleviate pain or discomfort. In comparison to the disc space between adjacent vertebrae, the space between the superior and inferior articular processes at the facet joint is relatively small, thereby leading to difficulties in accessing and positioning an implant within the space. Moreover, the anatomy and size of the space between the superior and inferior articular processes at the facet joints can limit the amount of bone growth promoting materials or grafts that can be positioned therebetween and/or result in the expulsion of at least some of the bone growth promoting materials therefrom. These and other factors may result in pseudarthrosis or inadequate stabilization or fusion of the facet joint. Thus, there remains a need for further improvements in the devices, instruments, assemblies, apparatuses, systems, and methods for performing facet joint stabilization and/or fusion techniques.

SUMMARY

In one embodiment, a method for stabilization of a facet joint of the spinal column includes forming a cavity between the adjacent bones defining the facet joint and positioning an implant in the cavity between the adjacent bones. In one aspect of this embodiment, the method also includes positioning a bone anchor across the facet joint and engaging the bone anchor with each of the adjacent bones to force the bones toward one another and clamp the implant therebetween. In a further aspect of this embodiment, the implant is a cancellous bone dowel and becomes fractured into several fragments upon being clamped between the adjacent bones and/or otherwise interacting with the bone anchor. However, different embodiments, forms and applications are also envisioned.

In another embodiment, a method for stabilizing a facet joint of the spinal column includes inserting a distal end of a guide instrument between adjacent bones forming the facet joint and providing a cannula including an elongate body extending between a proximal end and a distal end. The method also includes distally advancing the cannula over the guide instrument. A reamer is inserted through the cannula and at least a portion of each of the adjacent bones is removed to form a cavity for receiving an implant in the facet joint between the adjacent bones. The implant extends between a proximal end and a distal end and includes a support body and a reduced diameter instrument engagement portion extending proximally from a proximally facing end wall of the support body. The method also includes engaging the implant with an insertion instrument and inserting the implant through the cannula and into the cavity.

In yet another embodiment, a system for stabilization of a facet joint of the spinal column includes an implant configured to be inserted between adjacent bones forming the facet joint. The system also includes a bone screw configured to extend transversely to the implant when the implant is inserted between the adjacent bones. The bone screw includes a distal threaded portion configured for engagement with a first one of the adjacent bones, a proximal threaded portion, and a clamping member movable along the proximal threaded portion toward the distal threaded portion. Additionally, movement of the clamping member along the proximal threaded portion toward the distal threaded portion when the distal threaded portion is engaged with the first one of the adjacent bones brings the adjacent bones together and thereby clamps the implant between the adjacent bones. In a further aspect of this embodiment, the implant is formed of cancellous bone and becomes fractured when it is clamped between the adjacent bones.

In a further embodiment, a method for stabilization of a facet joint of the spinal column includes forming a cavity between adjacent bones defining the facet joint for receiving an implant in the facet joint, inserting the implant into the cavity, boring a hole extending transversely to the cavity through a first one of the adjacent bones and at least partially into a second one of the adjacent bones, and positioning a bone anchor in the hole and engaging the bone anchor with the first and second ones of the adjacent bones. In a further aspect of this method, engaging the bone anchor with the first and second ones of the adjacent bones includes forcing the first and second ones of the adjacent bones toward one another and clamping the implant between the adjacent bones. In another aspect, the implant is formed of cancellous bone and clamping the implant with the adjacent bones includes fracturing the cancellous bone into a plurality of fragments. In still another aspect of this embodiment, the method also includes boring the hole through a portion of the implant and positioning a portion of the bone anchor through the implant.

In still another embodiment, a method for promoting stabilization and fusion of a facet joint of the spinal column includes positioning a cancellous bone dowel between adjacent bones forming the facet joint and fracturing the cancellous bone dowel between the adjacent bones into a plurality of fragments. In one aspect of this embodiment, fracturing the cancellous bone dowel includes clamping the cancellous bone dowel between the adjacent bones.

Another embodiment of the present application comprises a unique system for performing facet joint stabilization and/or fusion in a patient. An additional embodiment of the present application comprises a unique implant and a corresponding set of unique instruments for accessing and preparing the facet joint for receipt of the implant and for delivering the implant to the facet joint. In one aspect of this embodiment, the instruments facilitate access and preparation of the facet joint and insertion of the implant through a minimally invasive approach that minimizes disruption and trauma to the tissues, muscles and other anatomical features located adjacent the facet joint.

Other embodiments include unique methods, systems, devices, kits, assemblies, equipment, and/or apparatus for use in connection with facet joint stabilization and/or fusion. However, in other embodiments, different forms and applications are also envisioned.

Further embodiments, forms, features, aspects, benefits, objects and advantages of the present application will become apparent from the detailed description and figures provided herewith.

DESCRIPTION OF THE ILLUSTRATED EMBODIMENTS

Figure 1:
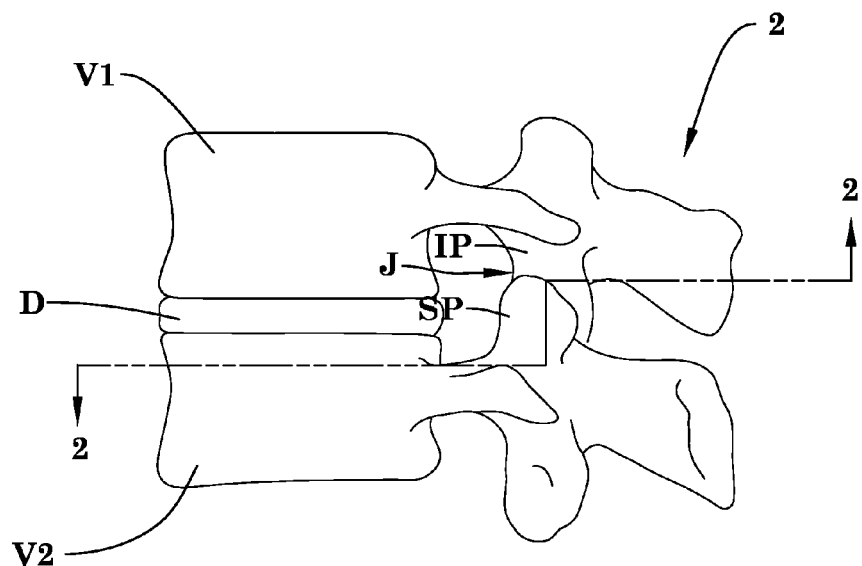
FIG. 1 is a side view of adjacent vertebrae of a spinal motion segment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments, devices, systems, apparatuses, assemblies, techniques and methods for performing spinal surgery, including but not limited to stabilization and/or fusion of one or more facet joints, are provided. More particularly, in one form, a method for stabilization of a facet joint of the spinal column includes forming a cavity between the inferior and superior articular processes defining the facet joint and positioning an implant in the cavity between the inferior and superior articular processes. In one aspect of this form, the method also includes positioning a bone anchor across the facet joint and engaging the bone anchor with each of the inferior and superior articular processes to force the bones toward one another and to clamp the implant therebetween. In a further aspect of this form, the implant is a cancellous bone dowel that becomes fractured into several fragments upon being clamped between the adjacent superior and inferior articular processes and/or otherwise interacting with the bone anchor. However, in other aspects of this form, the implant can be formed of a different material including but not limited to cortical bone or other types of bone growth promoting materials. In another form, systems and devices for performing percutaneous facet joint stabilization and/or fusion are provided. Still, it should be appreciated that alternative forms, aspects, configurations, arrangements and methods are contemplated with respect to the subject matter disclosed and described herein.

Figure 2:
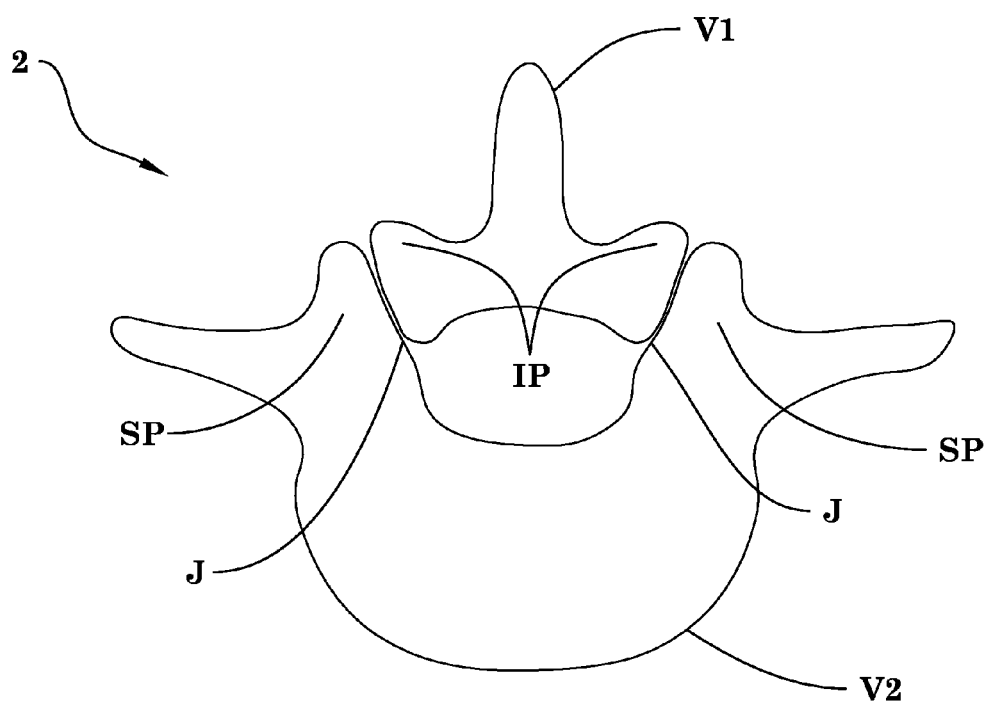
FIG. 2 is a section view taken along section line 2-2 of FIG. 1.

As indicated above, in certain aspects of the present application, the subject matter disclosed herein is related to stabilization and/or fusion of a facet joint of the spinal column, although application of the subject matter disclosed and described herein to additional or alternative locations of the spinal column or other anatomical areas of the body is also contemplated. To provide a better understanding of the anatomy of a facet joint of the spinal column, FIGS. 1 and 2 illustrate the relationship between adjacent vertebrae that define a pair of facet joints positioned on opposite lateral sides of the spinal column midline. More particularly, with reference to FIG. 1, illustrated therein is a side view of a spinal motion segment 2 that includes a first vertebra V1, a second vertebra V2, and an intervertebral disc D disposed therebetween. As shown in FIG. 2, the facet joints J of the spinal motion segment 2 are defined between the inferior articular process IP of the superior vertebra V1 and the superior articular process SP of the inferior vertebra V2.

Figure 3:
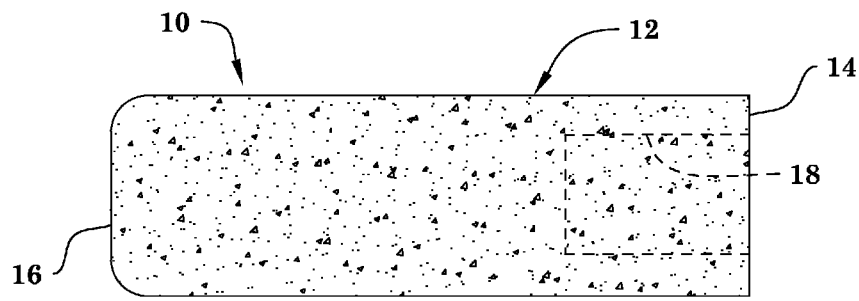
FIG. 3 is a side view of one embodiment of an implant configured for positioning in a facet joint.

With reference to FIG. 3, illustrated therein is one embodiment of an implant 10 sized and configured to be at least partly positioned in the facet joint J between the inferior articular process IP and the superior articular process SP. The implant 10 includes a body 12 extending between a proximal end 14 and a distal end 16. In one or more non-illustrated forms, the body 12 of the implant 10 may be provided with one or more bone engaging features, including but not limited to teeth, ridges, grooves, or spikes. Additionally, it is also contemplated that the body 12 can be tapered between the proximal end 14 and the distal end 16. In the illustrated form, the body 12 comprises a bone dowel formed from cancellous bone, although in other forms the body 12 may be formed of other bone growth promoting materials or other biologically compatible materials including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities. The body 12 also includes an internal cavity 18 that opens at the proximal end 14 and extends toward the distal end 16. The internal cavity 18 is generally configured to receive the distal end of an insertion instrument, such as the insertion instrument 20 illustrated in FIG. 4, the details of which are provided below. In addition to the cavity 18, it is also contemplated that the body 12 of the implant 10 may be provided with one or more additional cavities or receptacles to receive a bone growth promoting material such as bone chips, bone morphogenetic protein (BMP), LIM mineralization proteins (LMPs), transforming growth factors, such as transforming growth factor-β (BGF-β) insulin-like growth factors, platelet-derived growth factors, fibroblast growth factors, or other similar bone growth factors.

Figure 4:
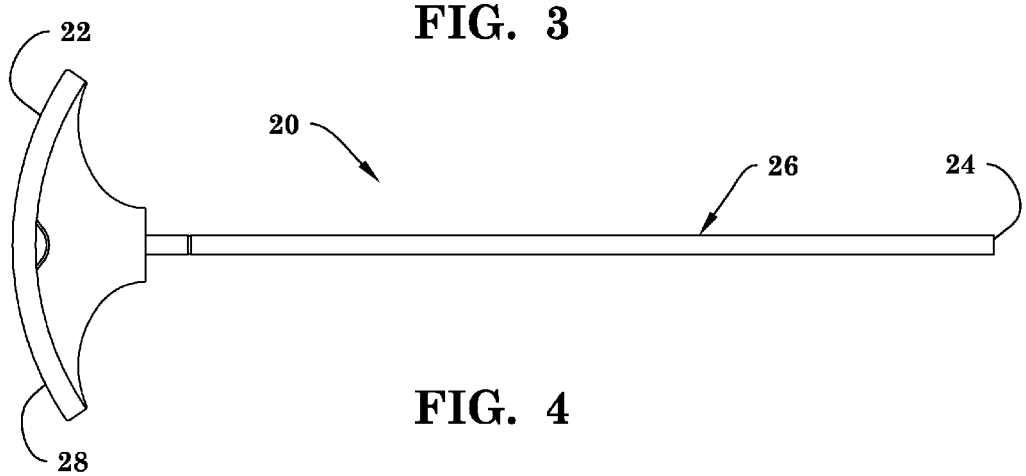
FIG. 4 is a side view of an insertion instrument for inserting the implant illustrated in FIG. 3.

As indicated above, the insertion instrument 20 illustrated in FIG. 4 is configured to engage with the cavity 18 of the implant 10. The insertion instrument 20 extends between a proximal end 22 and a distal end 24. A handle member 28 configured to be gripped by a surgeon or other medical personnel is positioned at the proximal end 22, and an elongated shaft 26 extends distally from the handle member 28. The shaft 26 at the distal end 24 and at least a portion thereof extending proximally from the distal end 24 is sized and shaped to be received in the cavity 18 of the implant 10. In one form, the cavity 18 and the shaft 26 are sized and shaped in a manner that results in a friction or press fit between the insertion instrument 20 and the implant 10 when they are coupled together such that the implant 10 will generally be retained on the insertion instrument 10 unless a sufficient separation force is applied to the two devices. In other non-illustrated forms, it is contemplated that one or both of the shaft 26 and the cavity 18 can be provided with surface features that facilitate releasable coupling of the insertion instrument 20 and the implant 10. For example, in one form, the shaft 26 may include external threading that is engageable with internal threading defined in the cavity 18.

Figure 5:
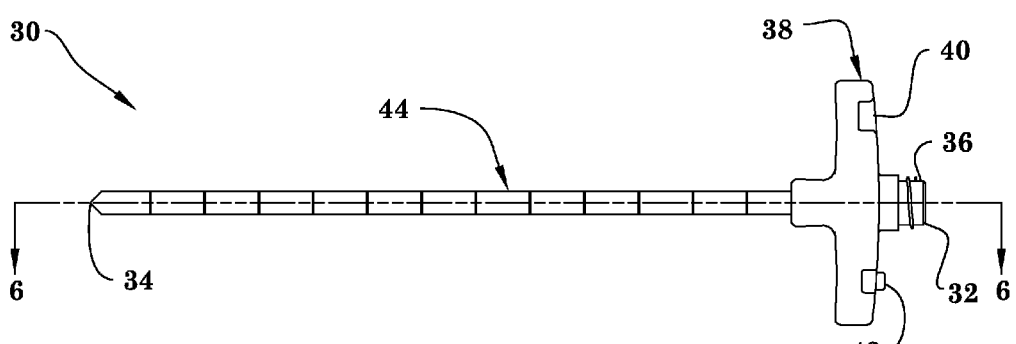
FIG. 5 is a side view of a cannula.
Figure 6:
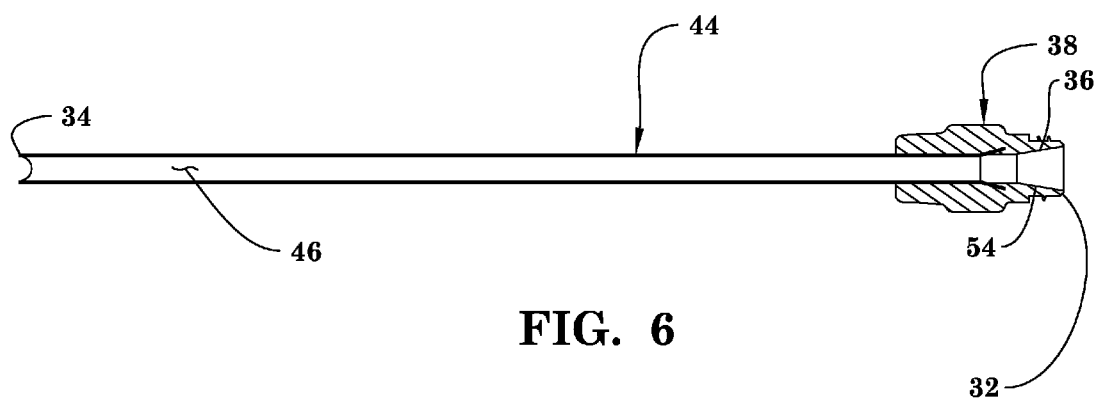
FIG. 6 is a section view of the cannula illustrated in FIG. 5 taken along view line 6-6 of FIG. 5.
Figure 7:
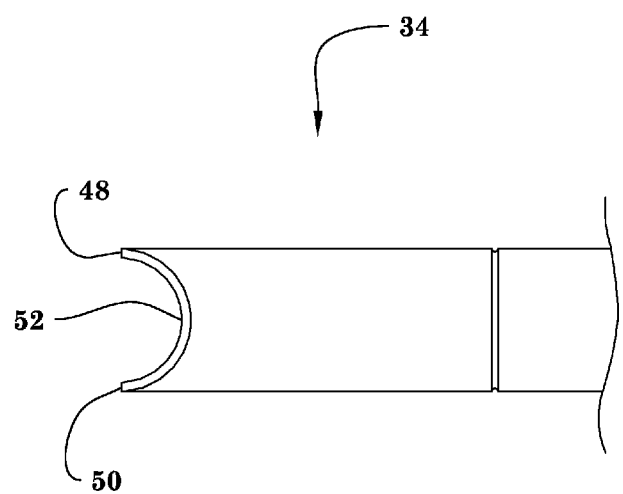
FIG. 7 is an enlarged view of the distal end of the cannula illustrated in FIG. 5.

A cannula 30 through which the implant 10 and a portion of the insertion instrument 20 can be positioned during implantation of the implant 10 at the facet joint J is illustrated in FIGS. 5-7. More particularly, the cannula 30 extends between a proximal end 32 and a distal end 34. The cannula 30 also includes an externally threaded portion 36 positioned between the proximal end 32 and a handle member 38 that is configured to be gripped by a surgeon or other medical personnel. The handle member 38 includes a pair of engaging portions 40, 42 which are positioned on a convexly curved, proximally facing surface and configured to facilitate releasable engagement of the cannula 30 with other instruments, such as the reamer 60 illustrated in FIGS. 8 and 9. An elongated tube member 44 extends distally from the handle member 38. As illustrated in the section view of FIG. 6, the elongated tube 44 includes a passageway 46 that extends between and opens at the proximal end 32 and the distal end 34 of the cannula 30. The passageway 46 includes a tapered section 54 adjacent the proximal end 32 which can facilitate guiding of instruments or implants into the passageway 46 as they are moved distally through the cannula 30.

As illustrated in the enlarged view of FIG. 7 (rotated ninety degrees relative to the view illustrated in FIG. 5), the distal end 34 of the cannula 30 includes a concave portion 52 extending between and defining a pair of oppositely positioned distal tips 48, 50. Moreover, as shown in FIG. 5, the elongated tube 44 tapers along the concave portion 52 to the distal tips 48, 50 such that the cannula 30 includes a tapered configuration along the distal end 34 in the plane illustrated in FIG. 5. The distal tips 48, 50 and the tapered configuration of the cannula 30 along the distal end 34 can, amongst other things, assist in positioning the distal end 34 of the cannula 30 in the facet joint J between the superior and inferior articular processes SP, IP.

Figure 8:
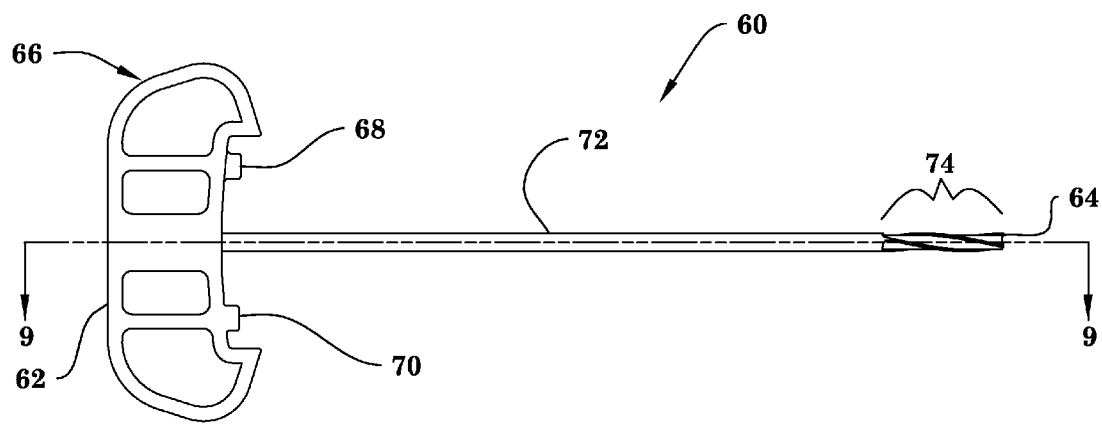
FIG. 8 is a side view of a reamer.
Figure 9:
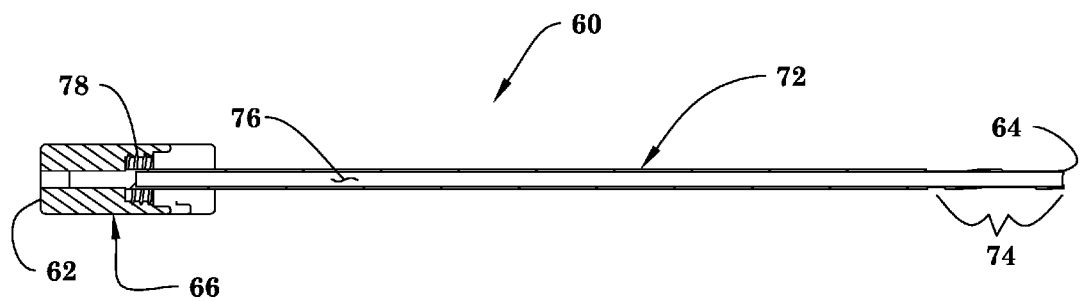
FIG. 9 is a section view of the reamer illustrated in FIG. 8 taken along view line 9-9 of FIG. 8.

Referring now to FIGS. 8 and 9, shown therein is one form of a reamer 60. The reamer 60 extends between a proximal end 62 and a distal end 64. A handle member 66 configured to be gripped by a surgeon or other medical personnel is positioned adjacent the proximal end 62. An elongated shaft 72 extends distally from the handle member 66 and includes a fluted cutting portion 74 that extends proximally from the distal end 64 toward the handle member 66. It should be appreciated that the fluted cutting portion 74 can be provided with any configuration suitable for cutting and removing bone and bony tissue. The elongated shaft 72 includes an axial passageway 76 that opens at and extends proximally from the distal end 64 into the handle member 66, although other embodiments where the passageway 76 extends through and opens at the proximal end 62 of the reamer 60 are also contemplated. The passageway 76 is generally sized and configured to facilitate positioning of the reamer 60 over a guidewire, details of which will be provided below.

Figure 10:
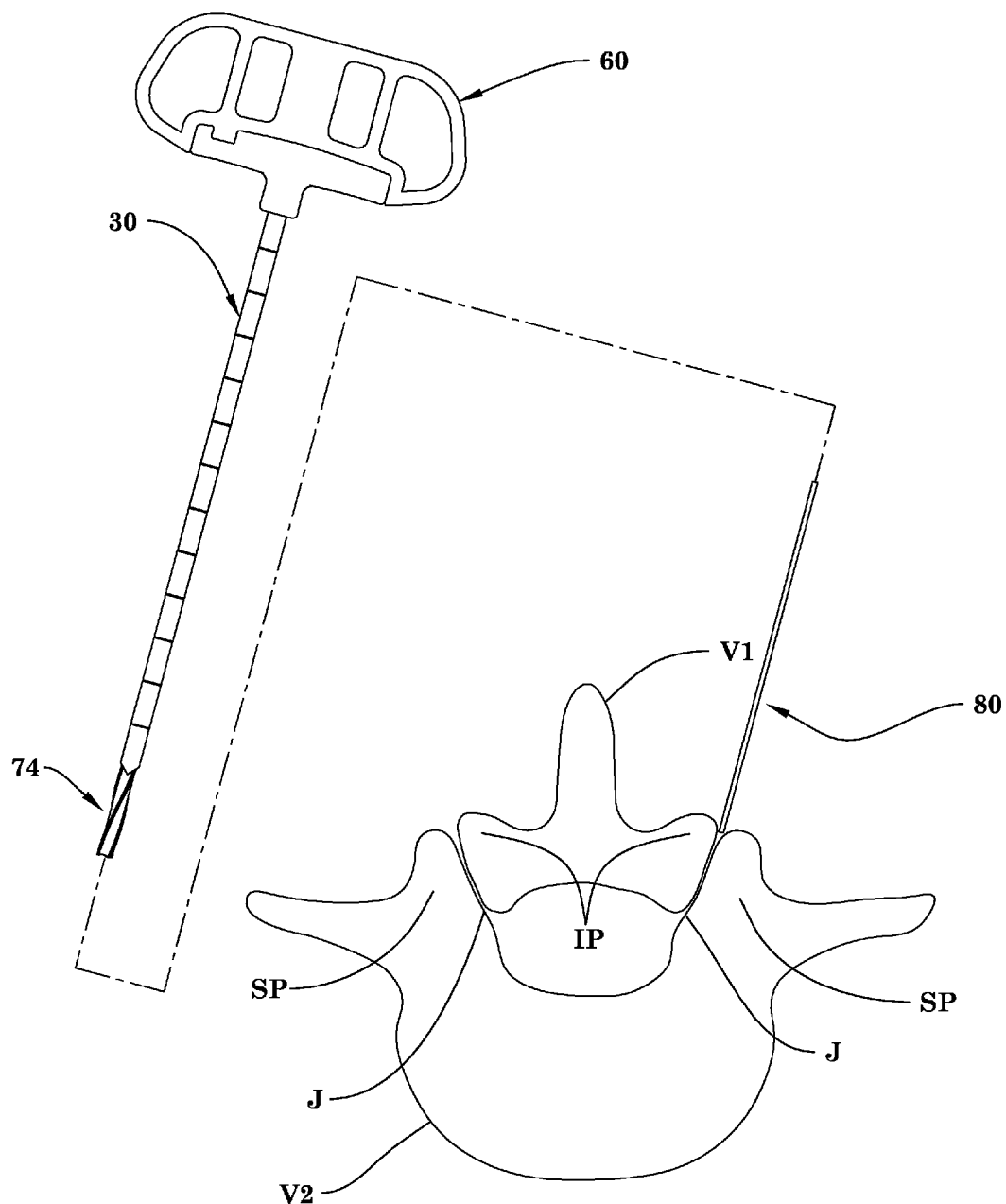
FIGS. 10-13 illustrate various steps of a surgical procedure for implanting the implant of FIG. 3 in a facet joint in a minimally invasive manner.

The elongated shaft 72 is generally sized to facilitate positioning of the elongated shaft 72 through the passageway 46 of the cannula 30. Moreover, the handle member 66 includes an internally threaded portion 78 that is engageable with the externally threaded portion 36 of the cannula 30 when the elongated shaft 72 is positioned in the passageway 46 of the cannula 30 in order to releasably couple the cannula 30 with the reamer 60. As illustrated in FIG. 10, when the cannula 30 and the reamer 60 are coupled together, at least a portion of the fluted cutting portion 74 of the reamer 60 extends distally beyond the distal end 34 of the cannula 30. The handle member 66 includes a concavely rounded distally facing surface that generally corresponds to the convexly rounded portion of the handle member 38 of the cannula 30. A pair of engaging portions 68, 70 are positioned on the distal facing surface and are configured to releasably engage the engaging portions 40, 42 of the cannula 30. Additionally, when the engaging portions 68, 70 are engaged with the engaging portions 40, 42, rotation of the reamer 60 relative to the cannula 30 is prohibited. In this configuration, rotation of one of the cannula 30 and the reamer 60 results in rotation of both of the cannula 30 and the reamer 60. However, the engaging portions 40, 42 and the engaging portions 68, 70 may be disengaged from one another to facilitate rotation of the reamer 60 relative to the cannula 30.

It should be appreciated that the insertion instrument 20, the cannula 30 and the reamer 60 may be made from any suitable biocompatible material, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities. Additionally, it is also contemplated that the insertion instrument 20, the cannula 30, and the reamer 60 may be configured for disposal after a single use or for cleaning and reuse. Other devices or instruments configured to be used with the cannula 30 in addition to the insertion instrument 20 and the reamer 60 include nerve root retractors, tissue retractors, forceps, cutters, scrapers, separators, rongeurs, taps, cauterization instruments, irrigation and/or aspiration instruments, and illumination instruments, just to new a few possibilities.

As indicated above, one particular application for the implant 10, the insertion instrument 20, the cannula 30, and the reamer 60 includes a procedure for stabilizing and/or fusing a facet joint J. With reference to FIGS. 10-13, illustrated therein is one method for positioning the implant 10 in a facet joint J between the superior and inferior articular processes SP, IP. However, it should be appreciated that while the implant 10 is described as being used in connection with a surgical procedure performed in relation to the facet joint J, implantation of the implant 10 at other locations along the spinal column or at other anatomical locations besides the spinal column are contemplated.

With reference to FIG. 10, a guidewire 80 is inserted through an incision in the skin and tissue (not shown) and advanced into or near one of the facet joints J from a generally posterior or postero-lateral approach. In one form, the skin and tissue can be sequentially dilated via a dilation instrument set (not shown) inserted over the guidewire 80 and including one or more tissue dilators of increasing size. The tissue dilators are inserted one over another to form a pathway through the skin and tissue to the facet joint J. In such procedures, the final dilator is retained in place while the other dilators are removed to leave the working channel of the last dilator open. However, it should be appreciated that insertion and positioning of the implant 10 without guidewires and dilators is also contemplated.

Figure 11:
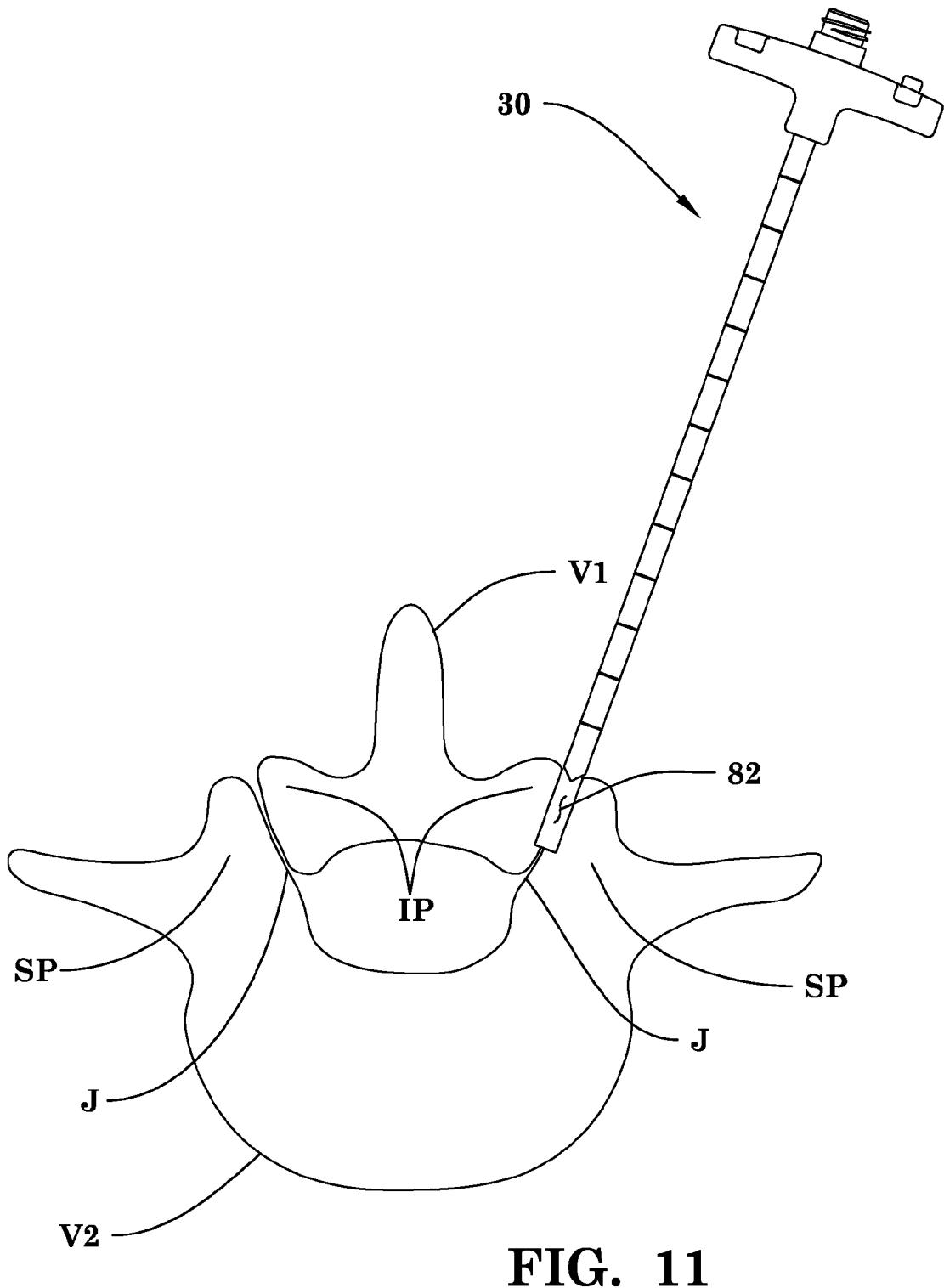

The cannula 30 and the reamer 60 are coupled together such that the fluted cutting portion 74 of the reamer 60 extends distally beyond the distal end 34 of the cannula 30, as illustrated in FIG. 10. When coupled together in this manner, the cannula 30 and the reamer 60 can be positioned within the remaining dilator, if present, with the guidewire 80 positioned in the passageway 76 of the reamer 60 in order to guide the cannula 30 and the reamer 60 to a location adjacent the facet joint J. Once the fluted cutting portion 74 of the reamer 60 contacts the superior and inferior articular processes SP, IP on opposite sides of the facet joint J, the cannula 30 and the reamer 60 can be rotated about the guidewire 80 in order to remove a portion of bone from each of the superior and inferior articular processes SP, IP so as to define a cavity 82 between the superior and inferior articular processes SP, IP at or near the facet joint J. As the fluted cutting portion 74 is rotated to form the cavity 82, the distal end 34 of the cannula 30 is partially advanced into the proximal end of the cavity 82 between the superior and inferior articular processes SP, IP, as illustrated in FIG. 11. Once the cavity 82 has been formed, the reamer 60 is disengaged and removed from the cannula 30. The guidewire 80 may also be removed. While not illustrated, it should be appreciated that the superior and inferior articular processes SP, IP can be distracted before the formation of the cavity 82 or following the formation of the cavity 82 but prior to the implant 10 being inserted in the cavity 82. In other forms, distraction of the superior and inferior articular processes SP, IP may not be necessary.

Figure 12:
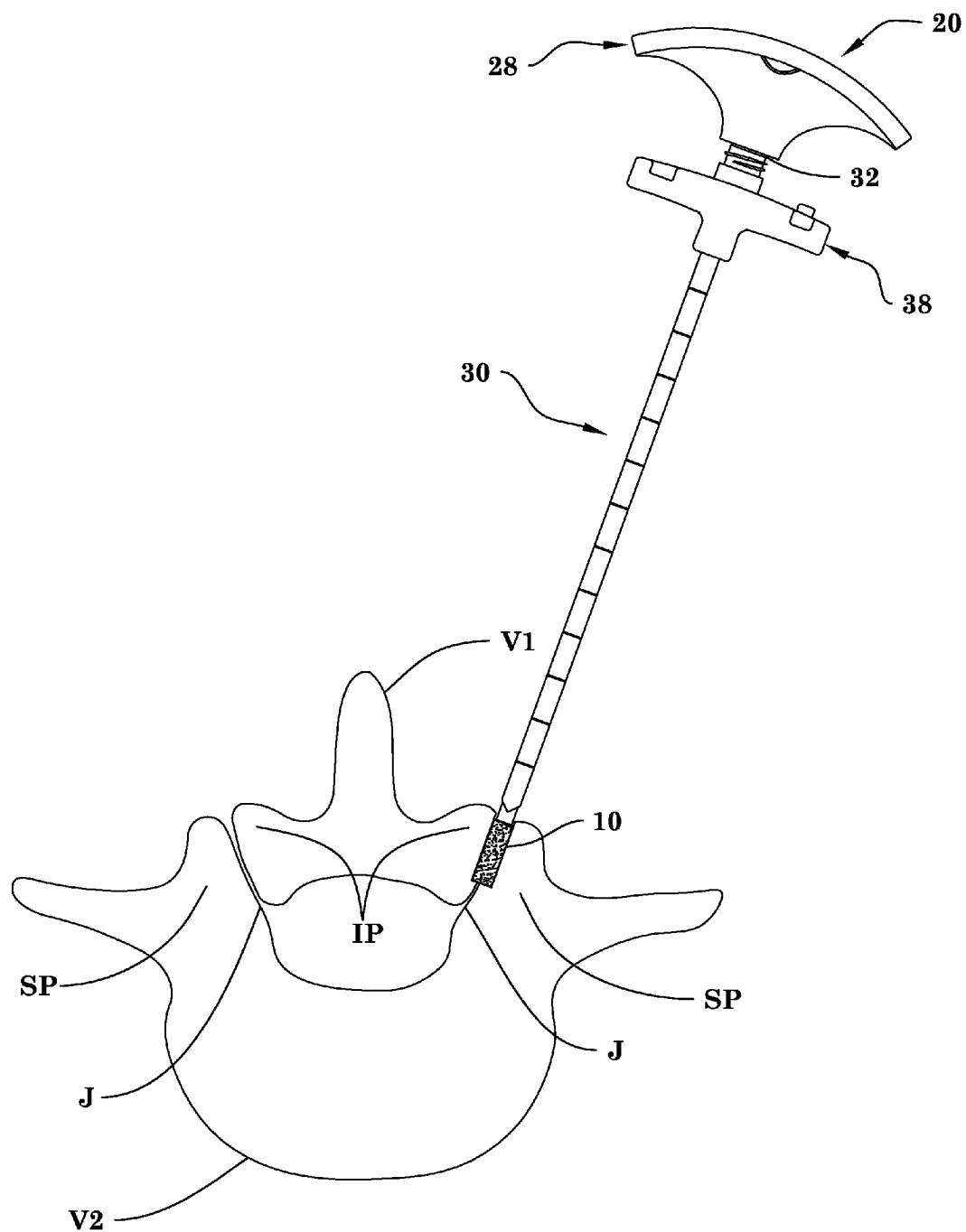
Figure 13:
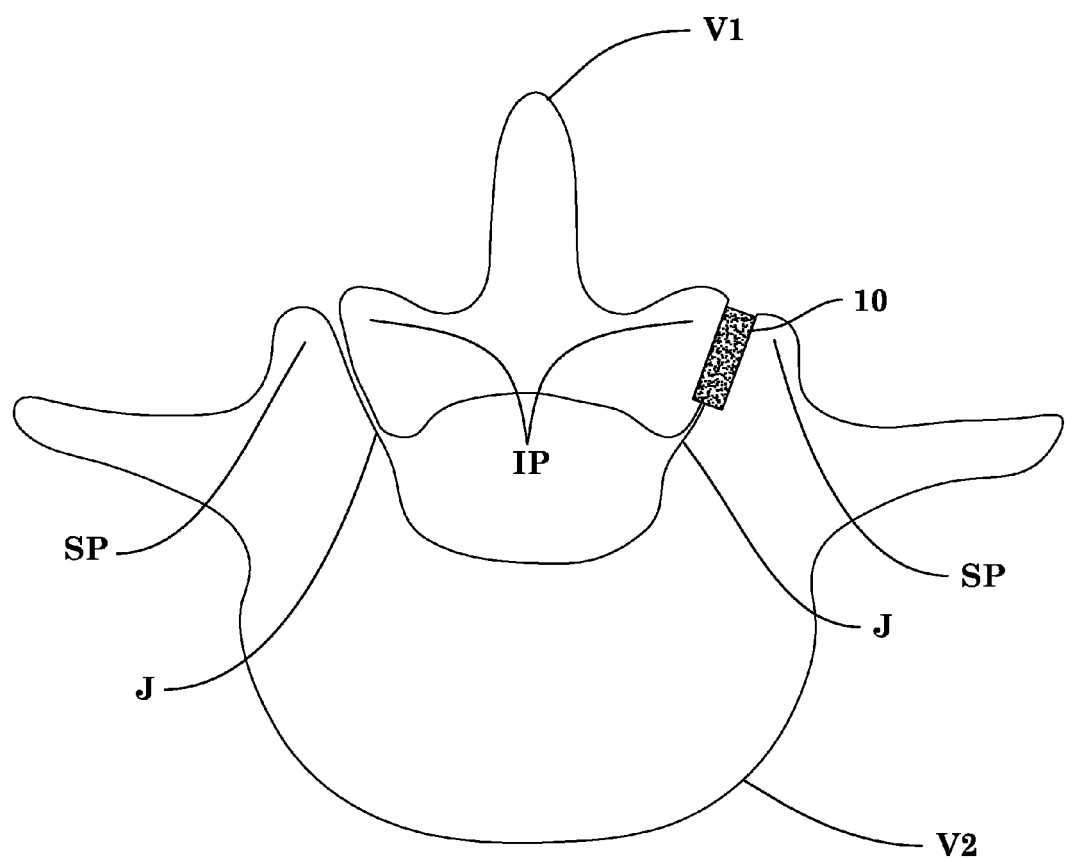

As illustrated in FIG. 12, the implant 10 is positioned on the distal end 24 of the insertion instrument 20 and is inserted through the passageway 46 of the cannula 30 and into the cavity 82. It should be appreciated that the cavity 82 and the implant 10 can be sized relative to one another such that a friction or press fit engagement is formed between the implant 10 and the cavity 82. However, in other forms, it is contemplated that the implant 10 may be loosely fit within the cavity 82. As also illustrated in FIG. 12, when the distal side of the handle member 28 contacts the proximal end 32 of the cannula 30, a portion of the insertion instrument 20 and the implant 10 are positioned distally of the distal end 34 of the cannula 30. Once the implant 10 has been properly positioned within the cavity 82, the insertion instrument 20 is disengaged from the implant 10 and proximally withdrawn from the cannula 30. The cannula 30 can also be removed from the facet joint J, thereby leaving only the implant 10 at the facet joint J, as illustrated in FIG. 13.

While not illustrated in FIGS. 10-13, it is also contemplated that the position of the implant 10 may be fixed relative to the superior and inferior articular processes SP, IP by a fastener engaged to one or both of the superior and articular processes SP, IP. Non-limiting examples of fasteners that may be used to secure the implant 10 within the cavity 82 include a pin, a nail, a screw, a staple, or a wedge, just to provide a few possibilities. Another more particular form of a fastener that may be used to secure the implant 10 is the bone anchor assembly 90 illustrated in FIGS. 14-18, although use of the bone anchor assembly 90 in other manners and at different locations of the spine and the body are also contemplated.

Figure 14:
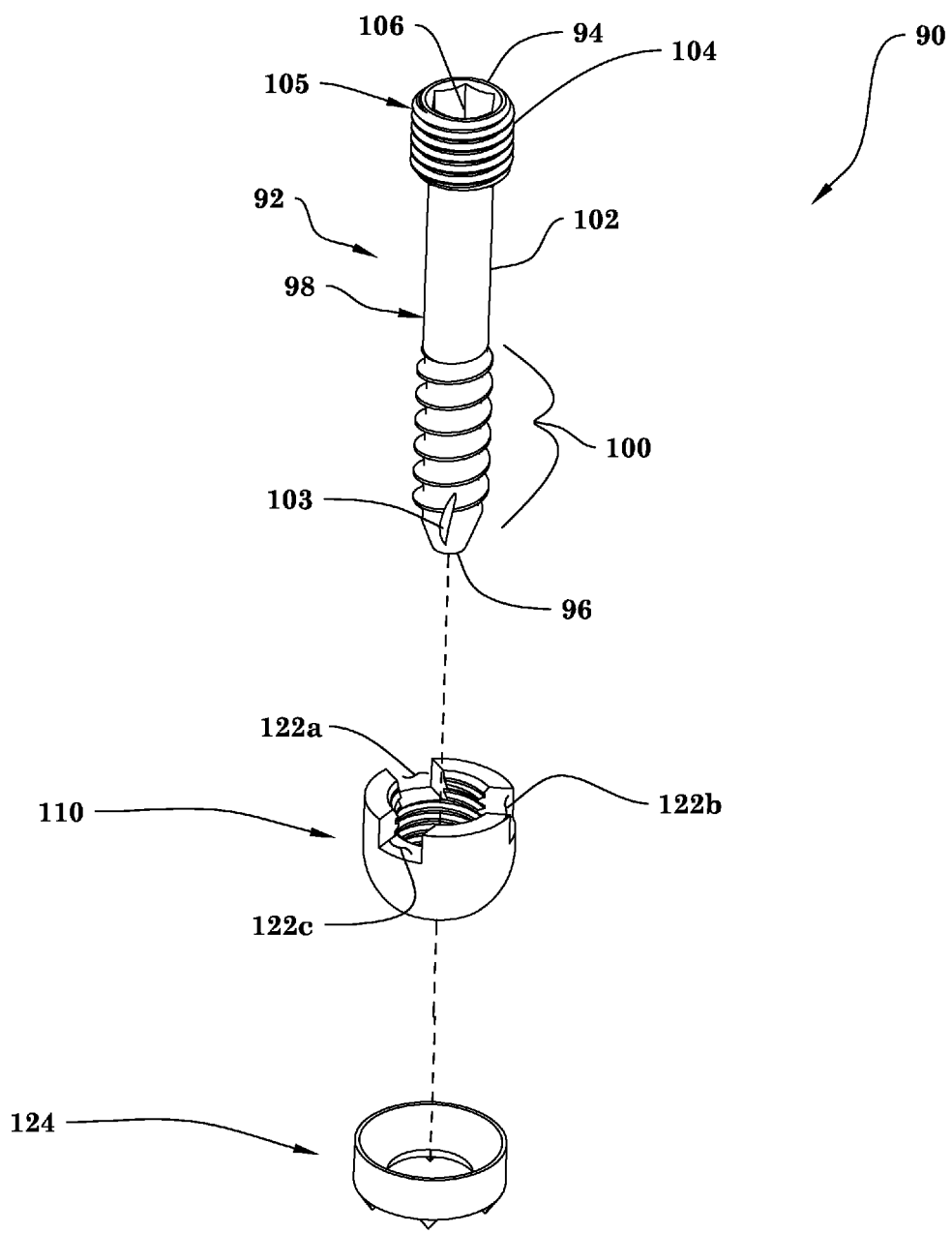
FIG. 14 is an exploded assembly view of a bone anchor assembly.

Referring generally to FIG. 14, the bone anchor assembly 90 includes a bone screw 92, a clamping member 110, and an engaging member 124. As will be discussed in greater detail below, the clamping member 110 and the engaging member 124 are positionable along the bone screw 92. The bone screw 92 extends between a proximal end 94 and a distal end 96 and includes an elongated shaft 98 extending distally from a head portion 105. The elongated shaft 98 includes a distal threaded portion 100 that is configured to engage with bone or bony tissue. More particularly, in the illustrated form, the distal threaded portion 100 includes a tapered or pointed section 101 to facilitate entry into bone. However, in other embodiments, the distal threaded portion 100 may define a blunt or rounded end. The distal threaded portion 100 may also be provided with a cutting flute 103 extending proximally from the distal end 96 to provide the bone screw 92 with self-cutting or self-tapping capabilities.

Figure 15:
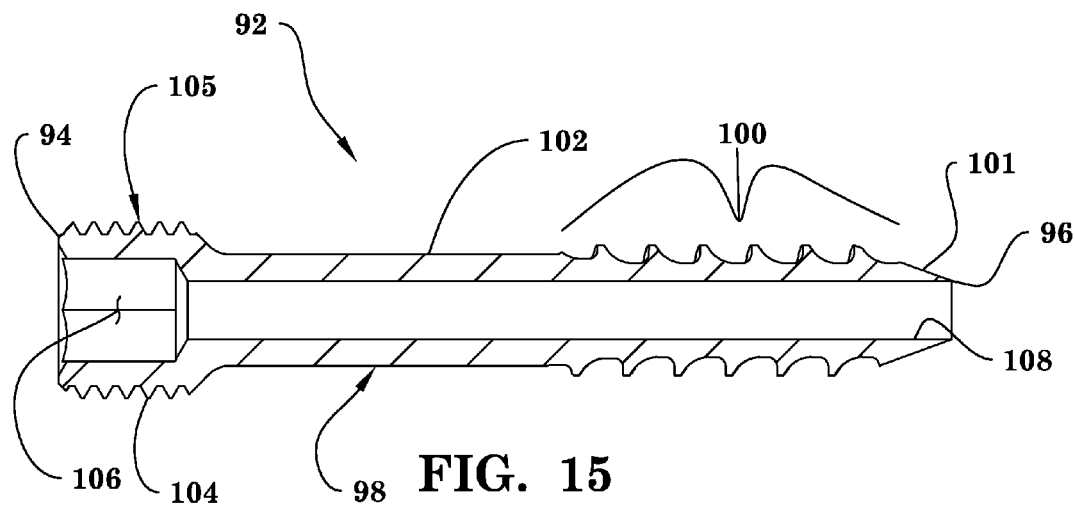
FIG. 15 is a section view of a bone screw of the bone anchor assembly illustrated in FIG. 14.
Figure 16:
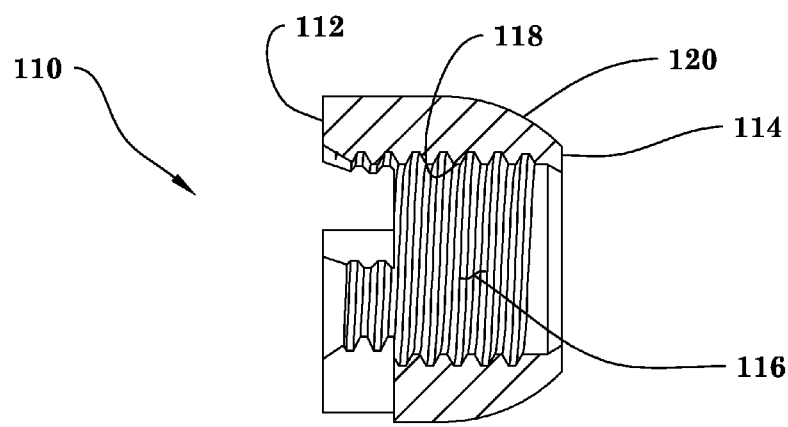
FIG. 16 is a section view of a clamping member of the bone anchor assembly illustrated in FIG. 14.
Figure 17:
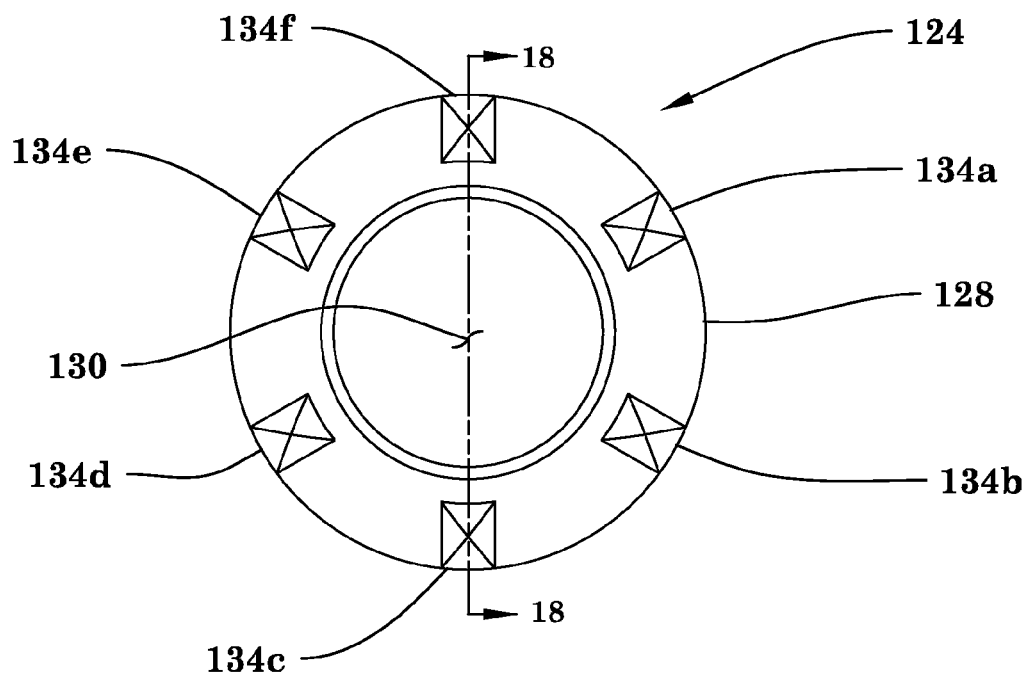
FIG. 17 is an end view of an engaging member of the bone anchor assembly illustrated in FIG. 14.
Figure 18:
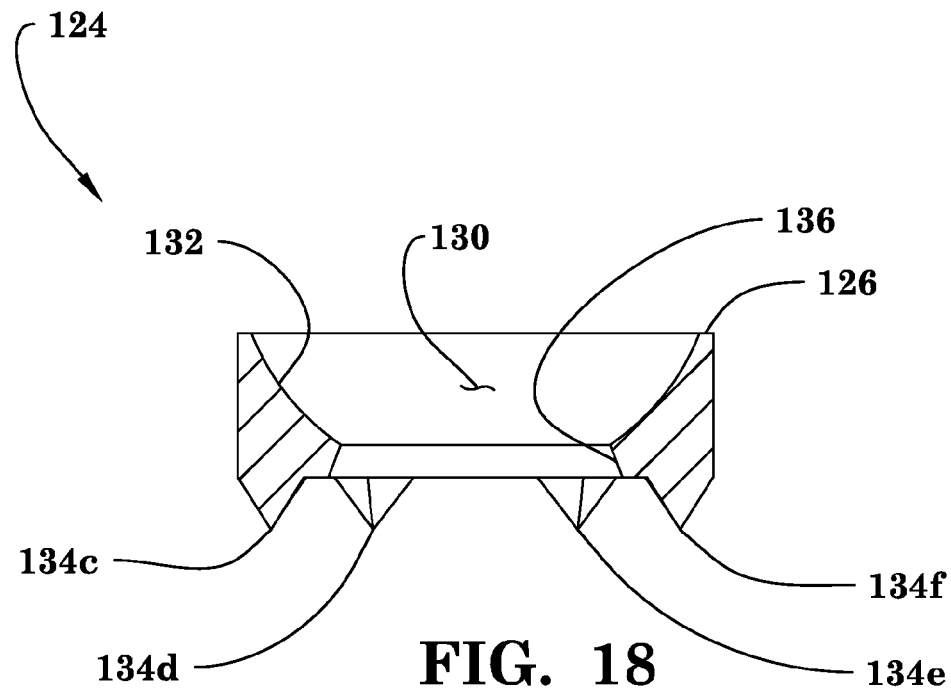
FIG. 18 is a section view of the engaging member illustrated in FIG. 17 taken along section line 18-18 of FIG. 17.

A non-threaded portion 102 extends between the distal threaded portion 100 and the head portion 105, although embodiments where the distal threaded portion 100 extends to the head portion 105 are also contemplated. The head portion 105 includes external threading 104 and an internal driving print 106 which may be non-circular such as, for example, hexagonal or rectangular shaped, to provide non-rotational engagement between the head portion 105 and a driving instrument (not shown) to rotatingly engage the bone screw 92 with bone or bony tissue. Examples of non-circular configurations for the driving print 106 include but are not limited to slotted, Phillips, hexagonal, Torx, spline drive, and double hex configurations. In addition, as illustrated in FIG. 15, the bone screw 92 includes a passageway 108 that extends between and opens at the proximal end 94 and the distal end 96. The passageway 108 can generally be sized and configured to allow placement of the bone screw 92 over a guidewire. Additionally or alternatively, the passageway 108 may communicate with fenestration openings (not shown) that may be used to deliver material such as, for example, bone cement from the passageway 108 and into areas of bone adjacent the bone screw 92.

The clamping member 110 extends between a proximal end 112 and a distal end 114 and includes a passage 116 that extends between and opens at the proximal end 112 and the distal end 114. The passage 116 includes internal threading 118 configured to cooperate and engage with the external threading 104 of the head portion 105. Similarly, when the clamping member 110 is engaged with the external threading 104 and rotated relative to the bone screw 92, its relative position along the length of the bone screw 92 is changed. The clamping member 110 also includes an arcuately rounded external portion 120 extending proximally from the distal end 114 such that the clamping member 110 includes a partially spherical external configuration. Additionally, the proximal end 112 also includes a plurality of notches 122a, 122b and 122c (FIG. 14) that are configured to facilitate engagement of the clamping member 110 by a driver instrument (not shown) suitable for rotating the clamping member 110 about the bone screw 92.

The engaging member 124 extends between a proximal end 126 and a distal end 128, with a plurality of engaging members in the form of spikes 134a-f extending from the distal end 128. In other forms, the distal end 128 can be provided with teeth, knurling, grooves or other types of engaging features in addition to or in lieu of the spikes 134a-f. The engaging member 124 also includes a passage 130 that extends between and opens at the proximal end 126 and the distal end 128. The passage 130 includes an arcuately rounded internal portion 132 extending distally from the proximal end 126 such that the engaging member 124 includes a partially spherical internal configuration. The passage 130 also includes a tapered portion 136 that is positioned distally of the arcuately rounded portion 132 and defines a diameter that is generally greater than the diameter of the non-threaded portion 102 of the bone screw 92 such that the engaging member 124 can be moved along the bone screw 92 and pivoted relative to the bone screw 92.

When the bone screw assembly 90 is assembled, the engaging member 124 may be positioned along the shaft 98 of the bone screw 92 distally of the head portion 105, and the arcuately rounded portion 120 of the clamping member 110 may be positioned in the arcuately rounded portion 132 of the engaging member 124. In this arrangement, the interaction between the arcuately rounded portions 120, 132 and the ability for the engaging member 124 to pivot relative to the bone screw 92 facilitates multi-axial positioning of the engaging member 124 in a plurality of planes that extend transversely to the plane of the clamping member 110 when engaged with the external threading 104 of the head portion 105. Similarly, this adjustability facilitates use of the bone anchor assembly 90 in connection with bones that are oriented at an angle relative to the head portion 105 of the bone screw 92. Moreover, while not previously discussed, it should be appreciated that the bone anchor assembly 90 can be implanted across adjacent bones or bone pieces and used to draw the adjacent bones or bone pieces toward one another. More particularly, once the distal threaded portion 100 of the bone screw 92 is engaged with a first one of the bones or bone pieces, the clamping member 110 can be rotated and distally advanced relative to the bone screw 92 in order to bring the engaging member 124 into contact with a second one of the bones or bony pieces. As the clamping member 100 is further rotated in this manner, the bones or bony pieces are drawn together and any gap positioned therebetween may be reduced or eliminated.

While not previously discussed, it should be appreciated that the bone screw 92, the clamping member 110, and the engaging member 124 may be formed from any suitable biocompatible material, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities.

Figure 19:
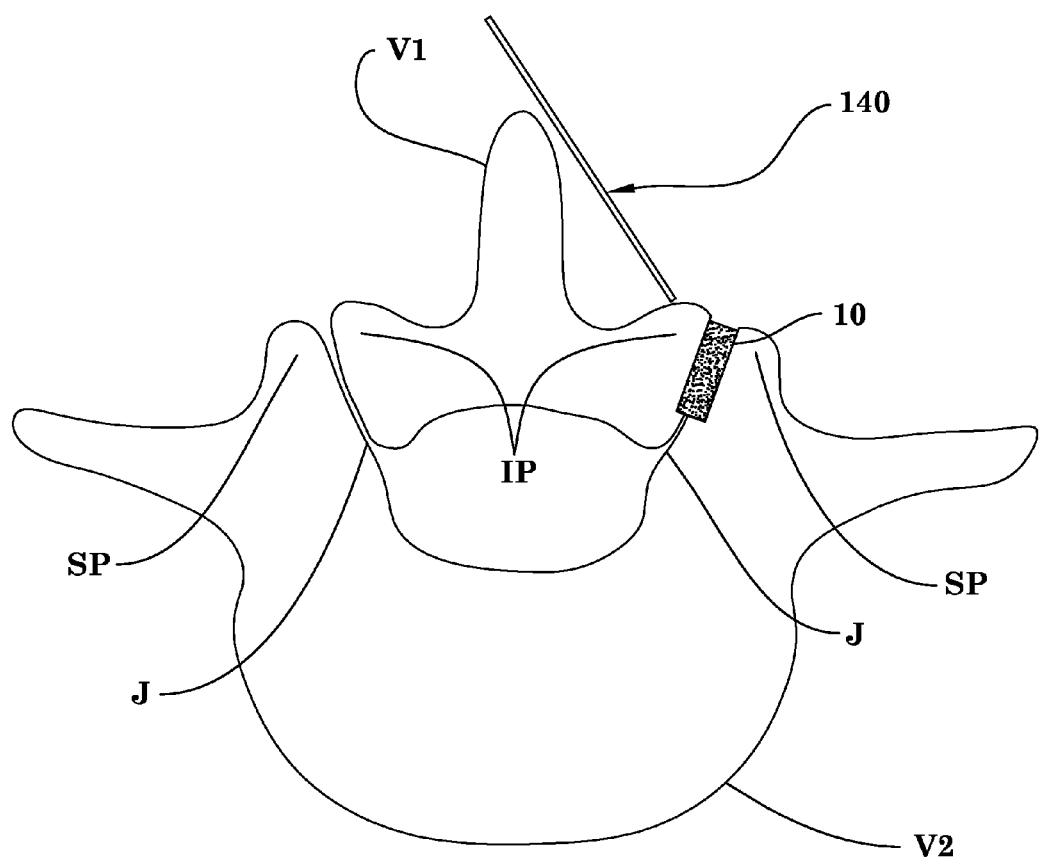
FIGS. 19-22 illustrate various steps of a surgical procedure for implanting the bone anchor assembly illustrated in FIG. 14 across a facet joint in which the implant illustrated in FIG. 3 is positioned.
Figure 20:
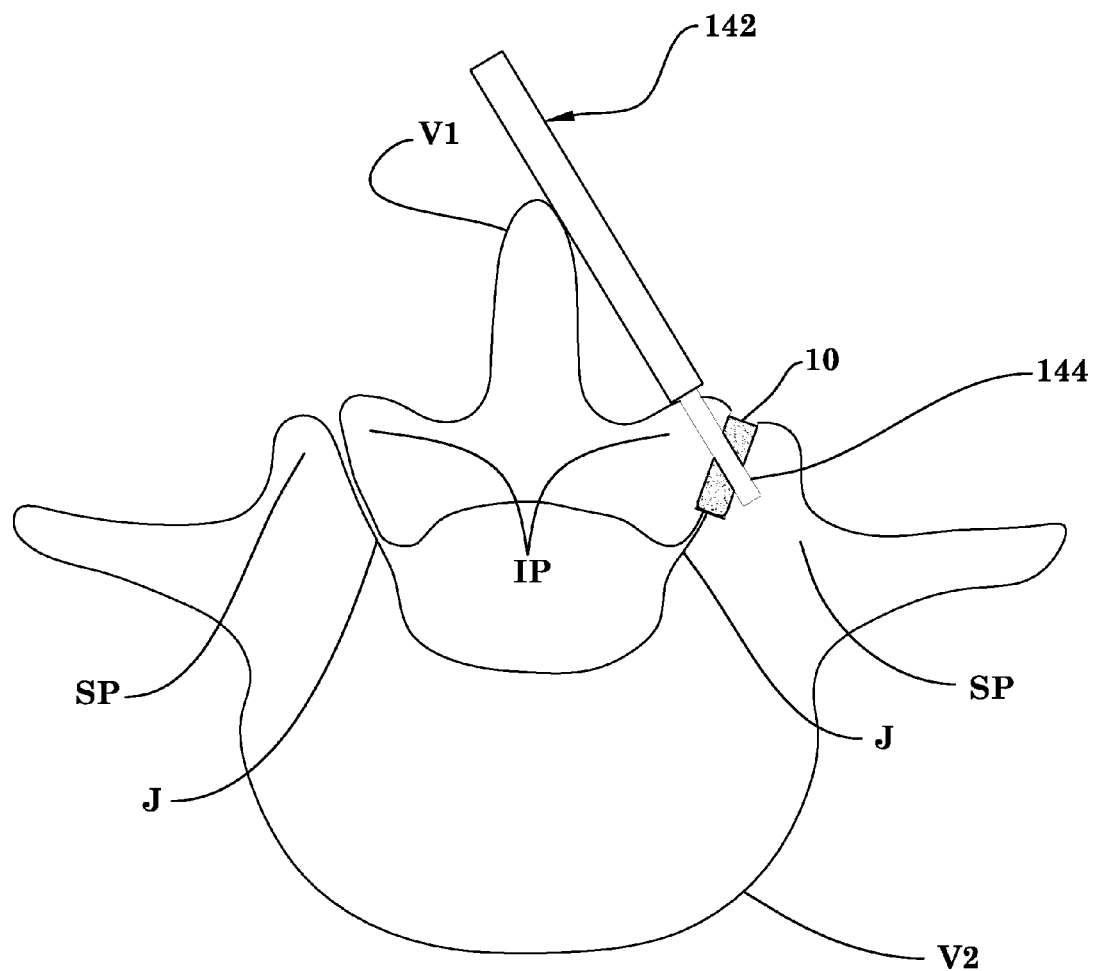
Figure 21:
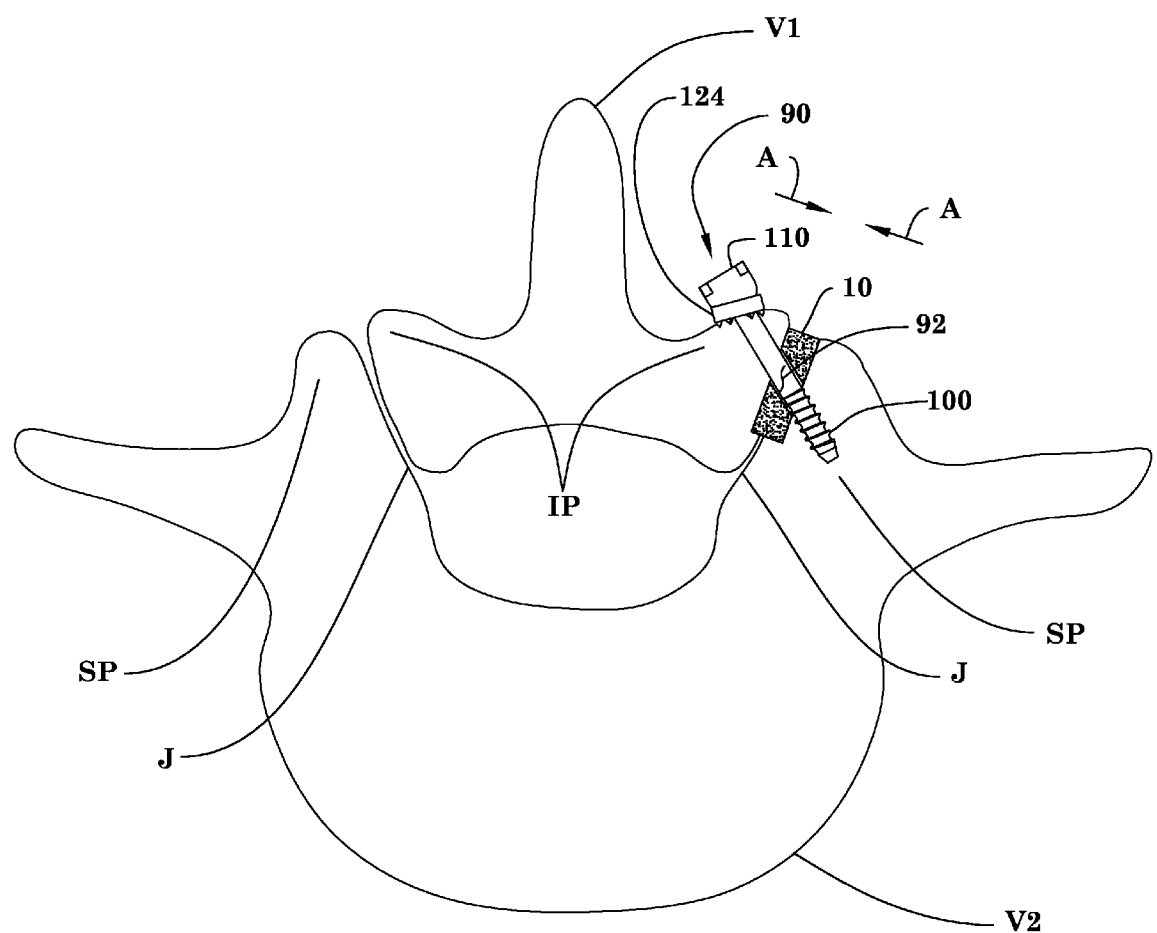

Referring now to FIGS. 19-22, one method for positioning the bone anchor assembly 90 across the facet joint J where the implant 10 has been implanted will now be described. With reference to FIG. 19, a guidewire 140 is inserted through an incision in the skin and tissue (not shown) and engaged with the inferior articular process IP of the vertebra V1 from a generally postero-medial approach such that the guidewire 140 extends transversely to the implant 10. In one form, the skin and tissue can be sequentially dilated via a dilation instrument set (not illustrated) inserted over the guide wire 140 and including one or more tissue dilators of increasing size. The tissue dilators are inserted one over another to form a pathway through the skin and tissue to the inferior articular process IP. A cannula 142 may be positioned over the last dilator and the other dilators and/or the guidewire 140 can be removed such that the cannula 142 provides an open working channel to the inferior articular process IP. However, it should be appreciated that insertion and positioning of the bone anchor assembly 90 without guidewires and dilators is also contemplated.

One or more drills, reamers or other cutting instruments (not shown) can be positioned through the cannula 142 to form a transverse hole 144 configured to receive the anchor assembly 90. In the illustrated form, the hole 144 extends through the inferior articular process IP of the vertebra V1, through the implant 10 positioned in the facet joint J, and partially into the superior articular process SP of the vertebra V2. In addition, the hole 144 generally extends obliquely to the implant 10 in a medial-lateral direction and may also extend obliquely to the implant 10 in a superior-inferior direction. In one form, it is contemplated that the implant 10 can be pre-formed with a hole that can be aligned with the hole 144 in order to eliminate drilling through the implant 10 in situ. Additionally, it should be appreciated that the hole 144 can be positioned differently in other non-illustrated forms. For example, in one form, the hole 144 can extend through the inferior articular process IP of the vertebra V1, across the facet joint J, and into the superior articular process SP of the vertebra V2 without extending through the implant 10.

Upon formation of the hole 144, the bone anchor assembly 90 can be positioned across the facet joint J. More particularly, the bone screw 92 can be engaged within the hole 144 such that the screw 92 extends through the inferior articular process IP of the vertebra V1 and into/through the implant 10. The distal threaded portion 100 of the bone screw 92 can then be engaged with the superior articular process SP of the vertebra V2 to secure the bone screw 92 in bone. Once the distal threaded portion 100 engages the superior articular process SP of the vertebra V2, the clamping member 110 can be distally advanced relative to the bone screw 92 until it engages with the engaging member 124 and forces the engaging member 124 against the exterior surface of the inferior articular process IP of the vertebra V1. As the clamping member 110 is advanced in this manner, the inferior and superior articular processes IP, SP are drawn together, as indicated by the directional arrows A in FIG. 21, and a clamping force is exerted onto the implant 10 positioned therebetween. This clamping force, in combination with the bone screw 92 extending through the implant 10, retains the implant 10 within the facet joint J. However, in other non-illustrated forms where the bone screw 92 does not extend through the implant 10, the clamping force alone exerted by the inferior and superior articular processes IP, SP retains the implant 10 within the facet joint J. In addition, in other non-illustrated forms it is contemplated that the bone screw 92 could be inserted through an opposite approach where it extends through the superior articular process SP, across the facet joint J, and into the inferior articular process IP.

Figure 22:
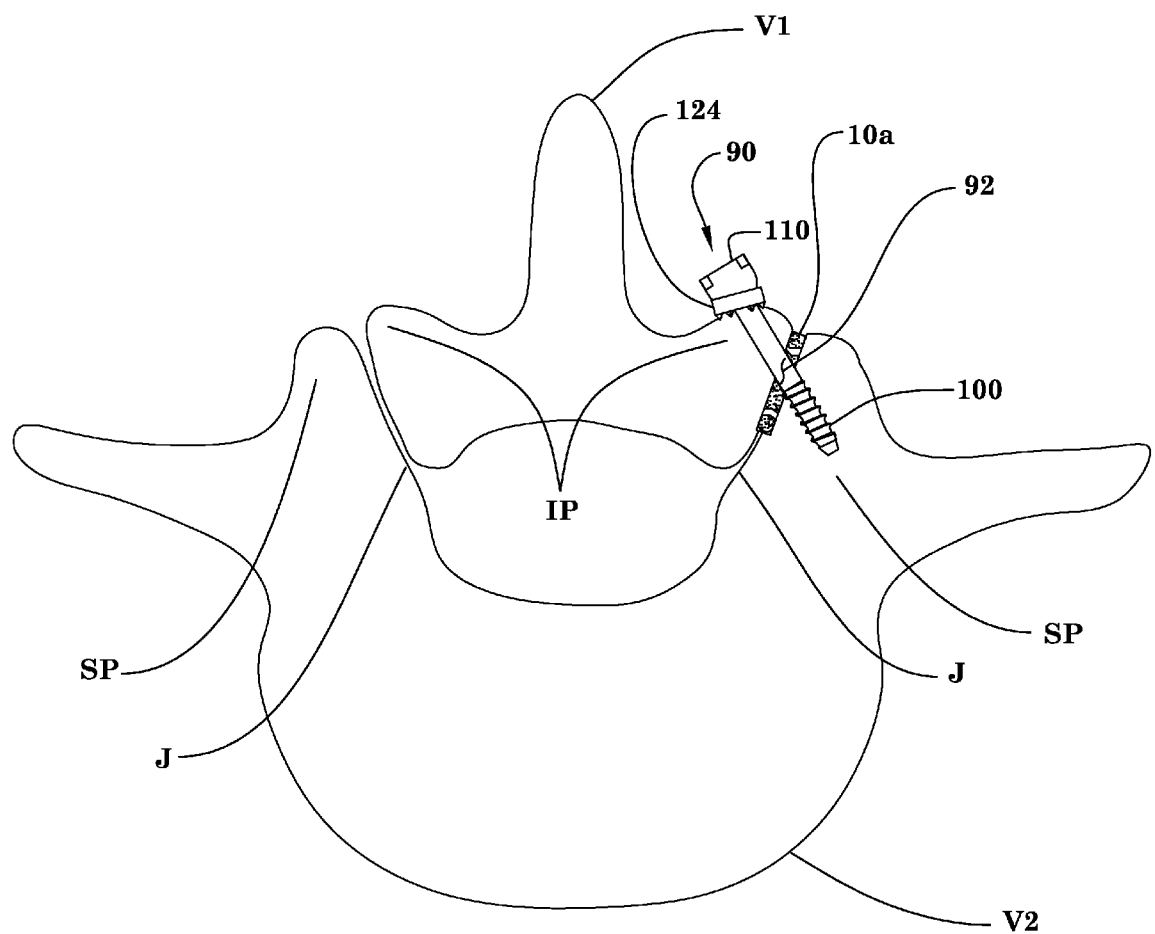

In one or more forms, it may be desirable to increase the clamping force exerted by the inferior and superior articular processes IP, SP onto the implant 10 until the cancellous bone from which the implant 10 is formed fractures into a plurality of fragments 10a, as illustrated in FIG. 22. Amongst other things, fracturing the implant 10 within the facet joint J in this manner can deliver and spread the cancellous bone across a relatively larger portion of the facet joint J which may otherwise be difficult to access, and thereby promote an increased likelihood of fusion between the inferior and superior articular processes IP, SP. Additionally, the clamping force exerted by the inferior and superior articular processes IP, SP can assist in retaining the cancellous bone fragments 10a within the facet joint J. In addition to or in lieu of fracturing the implant 10 via the clamping force exerted by the inferior and superior articular processes IP, SP, it is contemplated that the bone screw 92 could apply a fracturing force onto the implant 10 as it is threaded through the hole 144 that extends through the implant 10.

Moreover, while not previously discussed, it should be appreciated that fracturing the implant 10 in forms where the implant 10 is not formed of cancellous bone are also contemplated. For example, in one non-illustrated form, the implant 10 can be formed from a mixture of a biologically acceptable binder material with bone chips and/or other bone growth promoting materials. In this form, the implant 10 includes a generally solid, single piece configuration upon implantation that becomes fractured upon the application of sufficient force from the inferior and superior articular processes IP, SP as they are brought together by the bone anchor assembly 90. As discussed above, the clamping force exerted by the inferior and superior articular processes IP, SP can also assist in retaining these fragments in the facet joint J.

Figure 23:
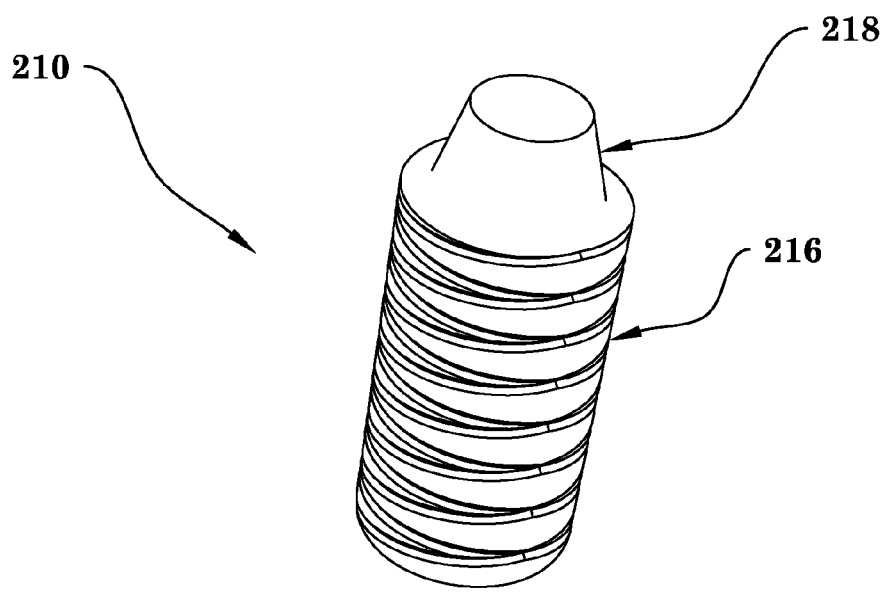
FIG. 23 is a perspective view of an alternative embodiment of an implant configured for positioning in a facet joint.
Figure 24:
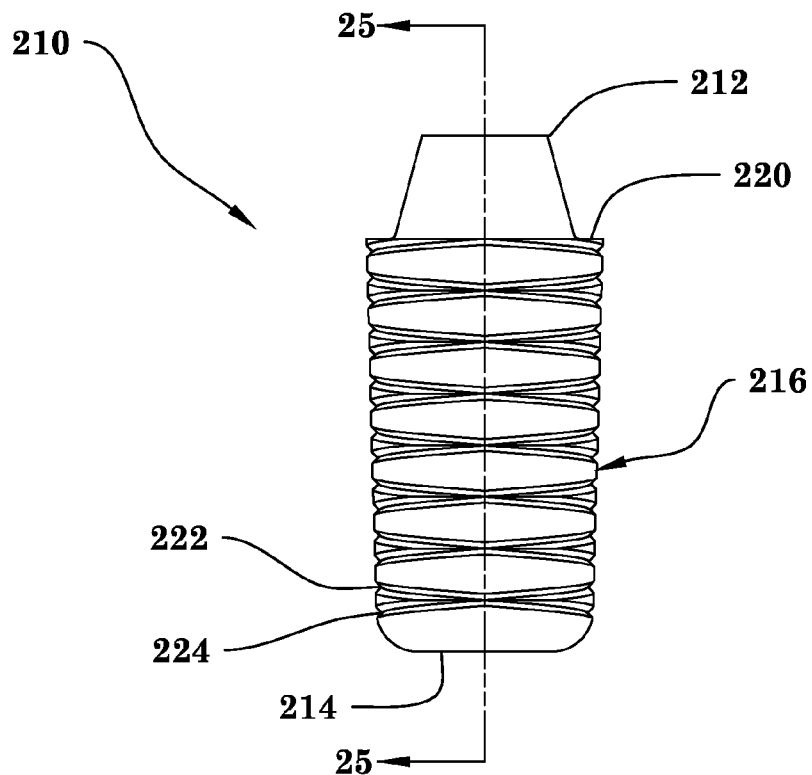
FIG. 24 is a side view of the implant illustrated in FIG. 23.
Figure 25:
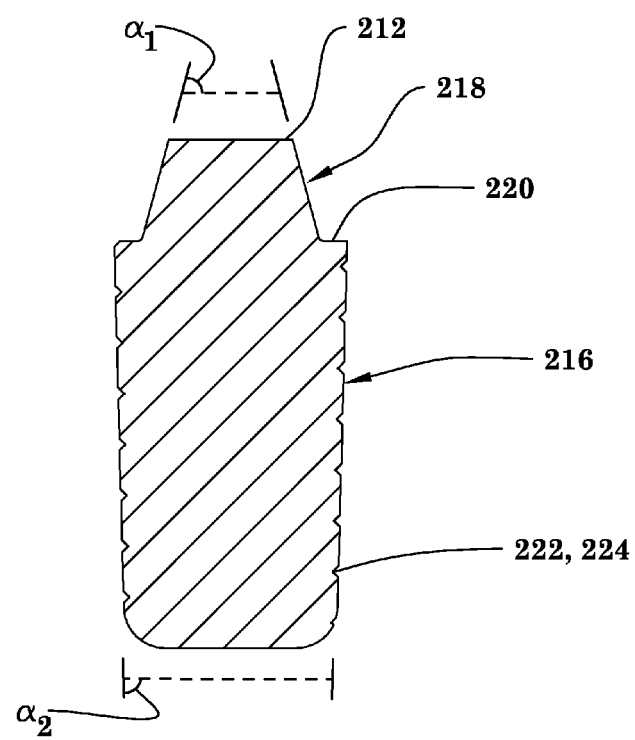
FIG. 25 is a section view of the implant illustrated in FIG. 24 taken along section line 25-25 of FIG. 24.

Referring now generally to FIGS. 23-25, an alternative embodiment implant 210 sized and configured to be positioned within the facet joint J between the inferior articular process IP and the superior articular process SP is illustrated. In one form, the implant 210 is formed of cortical bone, although forms in which the implant 210 is formed of other biologically compatible materials including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities, are also contemplated. The implant 210 extends between a proximal end 212 and a distal end 214 and includes a support body 216 configured to engage with the superior and inferior articular processes SP, IP. A tool engagement portion 218 having a reduced diameter and smaller configuration relative to the support body 212 extends proximally from a proximally facing end wall 220 of the support body 212. Similarly, the end wall 220 general defines a ledge that extends laterally beyond and radially about the base of the tool engagement portion 218. As shown in FIG. 25, the tool engagement portion 218 tapers proximally from the end wall 220 to the proximal end 212 at a first angle $\alpha_1$, while the support body 216 tapers distally from the end wall 220 to the distal end 214 at a second angle $\alpha_2$ which is generally smaller than the first angle $\alpha_1$. More particularly, in one form, the first angle $\alpha_1$ may be from about 10 to about 50 degrees, while the second angle $\alpha_2$ may be from about 1 to about 10 degrees, although it should be appreciated that alternative values for the first and second angles $\alpha_1$, $\alpha_2$ are contemplated.

The implant 210 also includes a pair of oppositely wound grooves 222, 224 that extend into and along the support body 216 from the distal end 214 to the end wall 220. The grooves 222, 224 are generally configured to enhance engagement of the support body 216 with the adjacent superior and inferior articular processes SP, IP in order to prevent expulsion of the implant 210 from the facet joint J. In other non-illustrated forms, it is contemplated that the support body 216 could be provided with one or more other bone engaging features in addition to or in lieu of the grooves 222, 224, including teeth, ridges, knurling, or spikes, just to name a few possibilities. As illustrated in FIGS. 24 and 25, due to the nature of being wound in opposite directions, the grooves 222, 224 come together at a first pair of opposite sides of the support body 216, but are partially separated from one another at a second pair of opposite sides of the support body 216 that are offset from the first pair of opposite sides of the support body 216. Additionally, it is also contemplated that the support body 216 of the implant 210 may also be provided with one or more cavities or receptacles to receive a bone growth promoting material such as bone chips, bone morphogenetic protein (BMP), LIM mineralization proteins (LMPs), transforming growth factors, such as transforming growth factor-β (BGF-β) insulin-like growth factors, platelet-derived growth factors, fibroblast growth factors, or other suitable bone growth factors.

Figure 26:
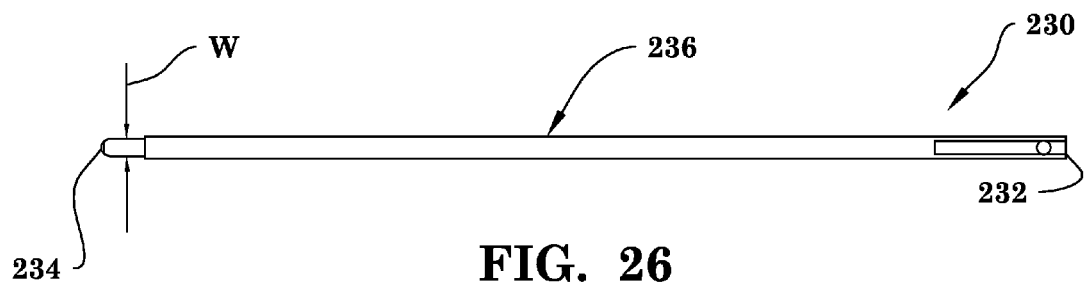
FIG. 26 is a top view of a guide instrument.
Figure 27:
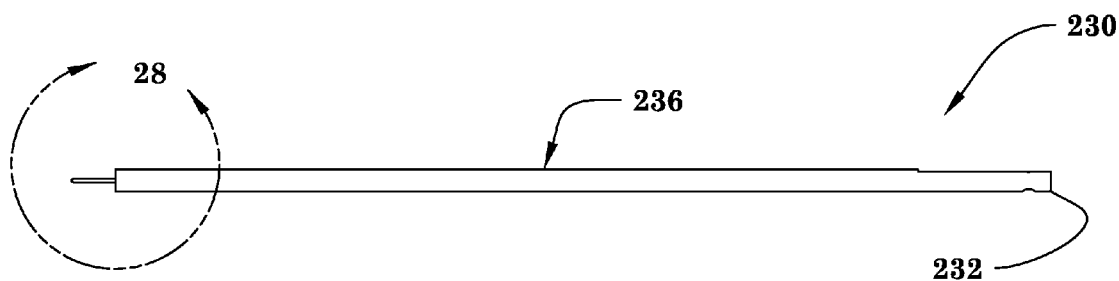
FIG. 27 is a side view of the guide instrument illustrated in FIG. 26.
Figure 28:
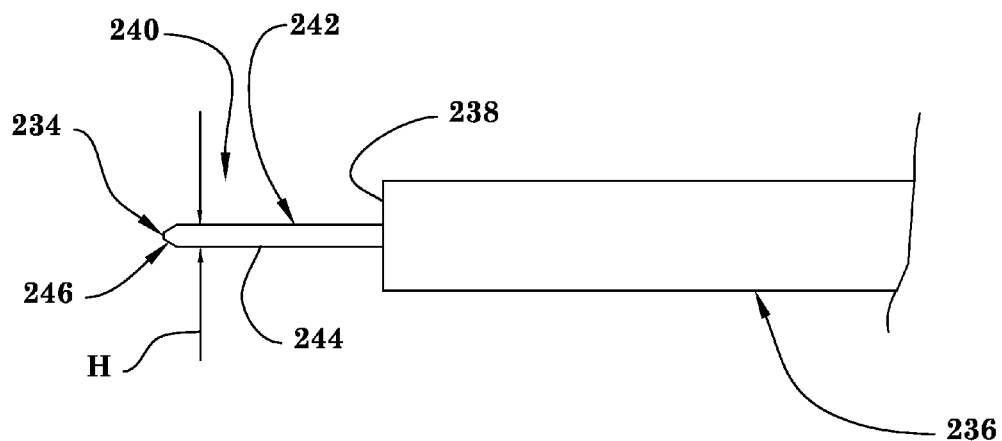
FIG. 28 is an enlarged side plan view of the distal end of the guide instrument illustrated in FIG. 27.

A guide instrument 230 that may be used during a surgical procedure for implantation of the implant 210 is illustrated in FIGS. 26-28. The guide instrument 230 extends between a proximal end 232 and a distal end 234 and includes an elongate shaft 236 extending from the proximal end 232 to a distally facing end wall 238. The elongate shaft 236 adjacent the proximal end 232 is generally configured for engagement with an impaction tool or other surgical instrument that can be used to position the distal end 234 of the guide instrument 230 within the facet joint J. Alternatively, it is contemplated that the elongate shaft 236 adjacent the proximal end 232 may be configured to be gripped by a surgeon or other medical personnel. A distal tip 240 extends distally from the end wall 238 to the distal end 234 and includes a pair of oppositely positioned surfaces 242, 244. While not illustrated, it is contemplated that the surfaces 242, 244 may each be roughened or may include cutting features to facilitate removal of tissue or cartilage between the superior and inferior articular processes SP, IP at or near the facet joint J.

The distal tip 214 also includes a tapered portion 246 adjacent the distal end 234 that can assist in guiding the distal tip 234 into the facet joint J. The surfaces 242, 244 are separated by a height H that is generally smaller than a width W extending laterally across the surfaces 242, 244. After the distal tip 240 is inserted in the facet joint J with the surfaces 242, 244 contacting the superior and inferior articular processes SP, IP, the guide instrument 230 can be rotated ninety degrees to distract the superior and inferior articular processes SP, IP if desired.

Figure 32:
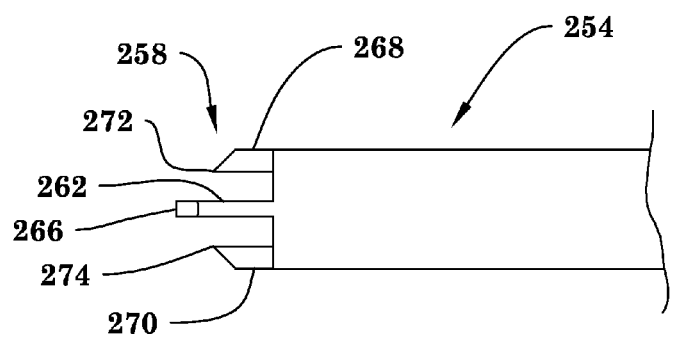
FIG. 32 is an enlarged side view of the distal end of the guide tube illustrated in FIG. 30 rotated ninety degrees relative to the view illustrated in FIG. 31.

Referring now to FIGS. 29-32, shown therein is a cannula 250 assembly that is positionable over the guide instrument 230 and through which the implant 210 can be positioned during a surgical procedure for implanting the implant 210 at or near the facet joint J. More particularly, the cannula assembly 250 includes a handle member 252 coupled with a guide tube 254. The guide tube 254 extends between a proximal end 256 to which the handle member 252 is coupled and a distal end 258. A passageway 259 extends through the guide tube 254 and opens at the proximal end 256 and the distal end 258, and is generally sized to facilitate positioning of the cannula assembly 250 over the guide instrument 230. The distal end 258 of the guide tube 254 includes a pair of oppositely positioned prongs 260, 262 that terminate distally at a pointed tip 264, 266, respectively. As illustrated in FIG. 32, a pair of oppositely positioned spikes 268, 270 are positioned between and offset from the prongs 260, 262. The spikes 268, 270 also terminate distally at pointed tips 272, 274, respectively.

Figure 29:
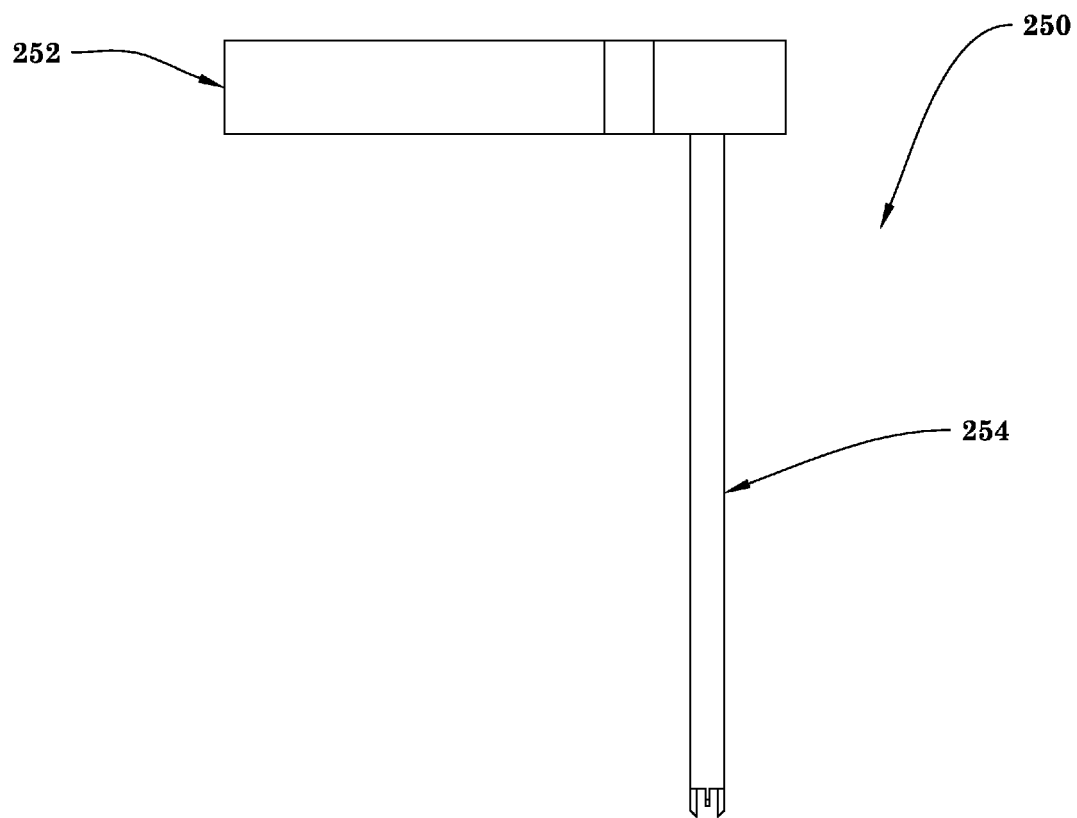
FIG. 29 is a side view of a cannula assembly.
Figure 30:
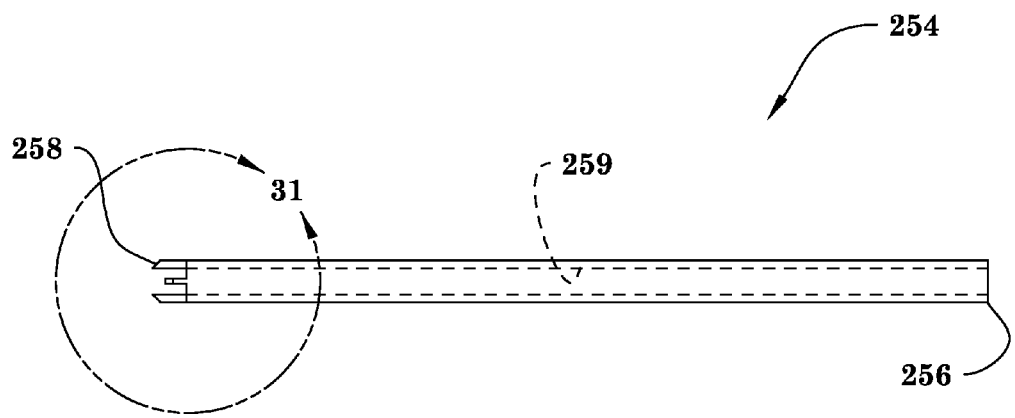
FIG. 30 is a side view of a guide tube of the cannula assembly illustrated in FIG. 29.
Figure 31:
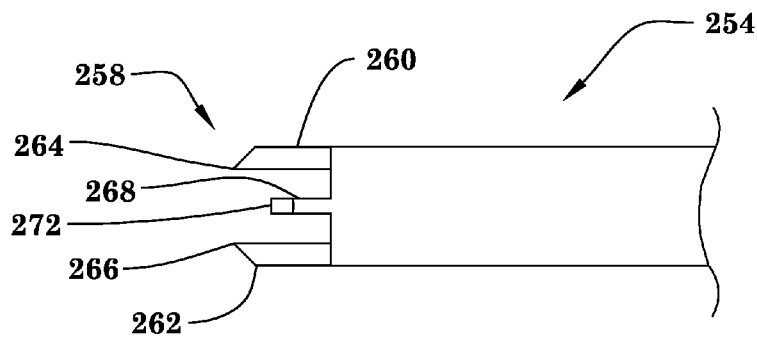
FIG. 31 is an enlarged side view of the distal end of the guide tube illustrated in FIG. 30.

The prongs 260, 262 are generally configured to be positioned between the superior and inferior articular processes SP, IP as the cannula assembly 250 is positioned over the guide instrument 230. As illustrated in FIG. 29, the handle member 252 is generally aligned with an axis extending between the prongs 260, 262, which amongst other things can indicate to a surgeon or other medical personnel the orientation of the prongs 260, 262 relative to the facet joint J. It should be appreciated that the prongs 260, 262 can generally extend inline with the lateral edges of the surfaces 242, 244 of the guide instrument 230 as they are positioned within the facet joint J. As the prongs 260, 262 are positioned within the facet joint J, the spikes 268, 270 come into contact and engage with the superior and inferior articular processes SP, IP to anchor the cannula assembly 250 relative to the facet joint J. In other forms, it is contemplated that the cannula assembly 250 can be rotated before the spikes 268, 270 engage with the superior and inferior articular processes SP, IP in order to distract the same.

Figure 33:
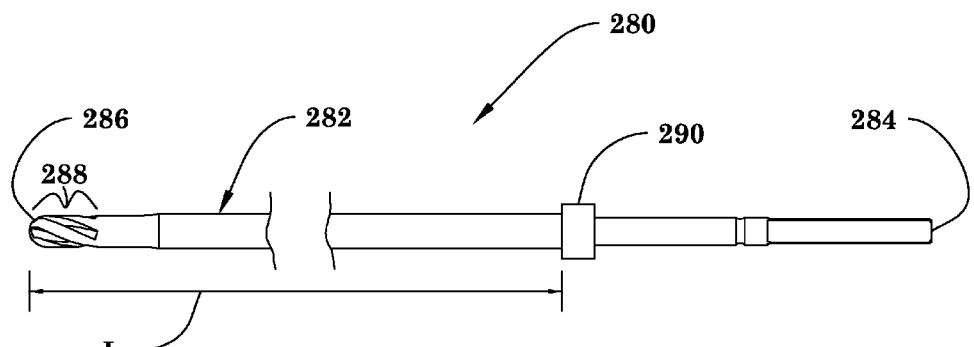
FIG. 33 is a side view of an alternative embodiment of a reamer.

A reamer 280 configured for use in association with the cannula assembly 250 is illustrated in FIG. 33. The reamer 280 includes an elongate shaft 282 that extends between a proximal end 284 and a distal end 286. The elongate shaft 282 is generally sized to facilitate positioning through the passageway 259 of the cannula assembly 250. Additionally, the elongate shaft 282 adjacent the proximal end 284 is configured for engagement with a driver or other surgical instruments that can be used to rotate the reamer to form a cavity between the superior and inferior articular processes SP, IP at or near the facet joint J. Alternatively, it is contemplated that the elongate shaft 282 adjacent the proximal end 284 may be configured to be gripped by a surgeon or other medical professional. The elongate shaft 282 also includes a fluted cutting portion 288 that extends proximally from the distal end 286. It should be appreciated that the fluted cutting portion 288 can be provided with any configuration suitable for cutting and removing bone and/or bony tissue.

A stop member 290 is positioned on the elongate shaft 282 between the fluted cutting portion 288 and the proximal end 284. The reamer 280 defines a length L between the stop member 290 and the distal end 286 such that the stop member 290 contacts the handle member 252 as the reamer 280 is positioned in the cannula assembly 250 in order to limit the distance which the fluted cutting portion 288 extends beyond the distal end 258 of the guide tube 254. Similarly, this arrangement can control the depth of the cavity formed between the superior and inferior articular processes SP, IP by the reamer 290. In one form, the position of the stop member 290 along the elongate shaft 282 is fixed such that the depth of the cavity formed with the reamer 280 is predetermined. However, in other forms, it is also contemplated that the stop member 290 can be adjustably movable along the elongate shaft 282 to allow a surgeon or other medical professional to selectively choose the depth of the cavity formed by the reamer 250.

Figure 34:
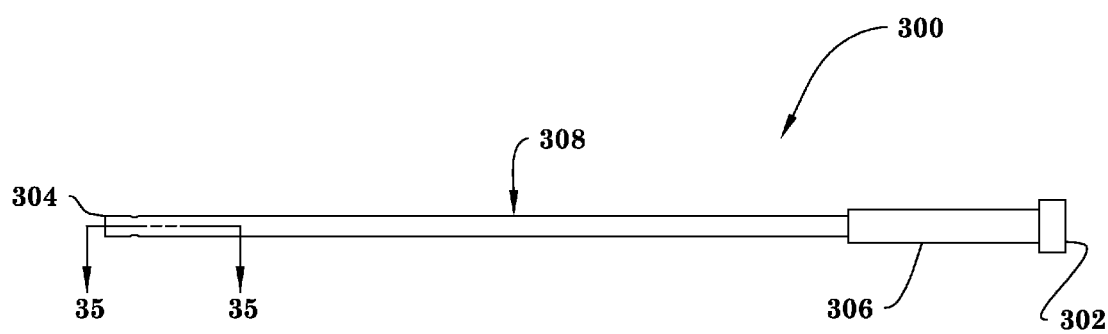
FIG. 34 is a side view of an insertion instrument for inserting the implant illustrated in FIGS. 23-25.
Figure 35:
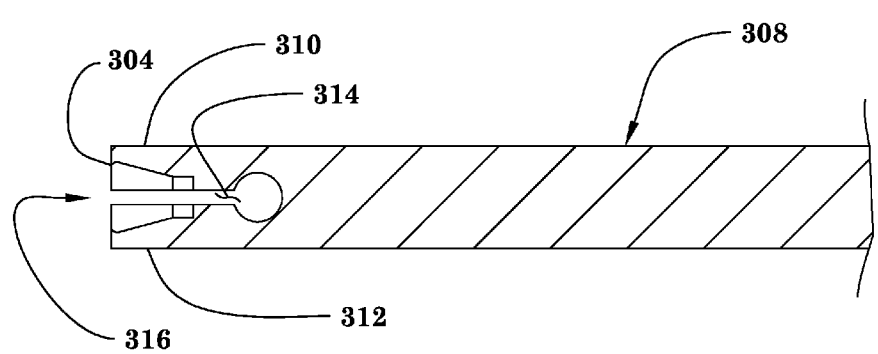
FIG. 35 is an enlarged section view of the distal end of the insertion instrument illustrated in FIG. 34 taken along section line 35-35 of FIG. 34.

Referring now to FIGS. 34 and 35, shown therein are details associated with an insertion instrument 300 configured for inserting the implant 210 in the facet joint J. The insertion instrument 300 extends between a proximal end 302 and a distal end 304. The insertion instrument 300 also includes a handle member 306 configured to be gripped by a surgeon or other medical personnel, and an elongate shaft 308 extending distally from the handle member 306 to the distal end 304. The distal end portion of the elongate shaft 308 is bifurcated into opposing portions 310, 312 adjacent the distal end 304, and a gap 314 is formed therebetween. A tapered receptacle 316 is also formed in and positioned between the portions 310, 312. The receptacle 316 is generally configured to receive the tool engaging portion 218 of the implant 210 in a friction or press fit arrangement. For example, the portions 310, 312 of the elongate shaft 308 may be resiliently flexible so as to exert a clamping force onto the tool engaging portion 218 of the implant 210 when positioned within the receptacle 316. Similarly, the implant 210 may generally be held within the receptacle 316 as the insertion instrument 300 and the implant 210 are positioned through the passageway 259 of the cannula assembly 250. In one form, the distal end 304 of the insertion instrument 300 may abut against the end wall 220 of the implant 210 when the tool engaging portion 218 is positioned within the receptacle 316, although forms where a gap exists between the distal end 304 and the end wall 220 are also contemplated.

Additionally, the elongate shaft 310 may be provided with an external diameter extending about the receptacle 316 when the tool engaging portion 218 of the implant 210 is positioned therein that closely matches the internal diameter of the passageway 259 such that the cannula assembly 250 prevents displacement of the portions 310, 312 away from one another when positioned within the passageway 259. This arrangement can assist in preventing disengagement of the implant 210 from the insertion instrument 300 when inserted through the cannula assembly 250. However, once the implant 210 is advanced distally beyond the distal end 258 of the guide tube 254 and into engagement with the superior and inferior articular processes SP, IP, the insertion instrument 300 can be proximally withdrawn from the cannula assembly 250 such that the implant 210 is released from the receptacle 316. In one or more non-illustrated forms, it is also contemplated that one or both of the tool engaging portion 218 and the receptacle 316 can be provided with surface features that facilitate releasable coupling of the insertion instrument 300 and the implant 210 in addition to or in lieu of the press-fit arrangement described above. For example, in one form, the tool engaging portion 218 may include external threading engageable with internal threading in the receptacle 316, although it should be appreciated that other arrangements are also contemplated.

It should be appreciated that the guide instrument 230, the cannula assembly 250, the reamer 280, and the insertion instrument 300 may be made from any suitable biocompatible material, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities. Additionally, it is also contemplated that the guide instrument 230, the cannula assembly 250, the reamer 280, and the insertion instrument 300 may be configured for disposal after a single use, or can be cleaned for reuse. Other devices or instruments that may be used in association with the cannula assembly 250 in addition to the guide instrument 230, the reamer 280 and the insertion instrument 300 include nerve root retractors, tissue retractors, forceps, cutters, scrapers, separators, rongeurs, taps, cauterization instruments, irrigation and/or aspiration instruments, and illumination instruments, just to provide a few examples.

Figure 36:
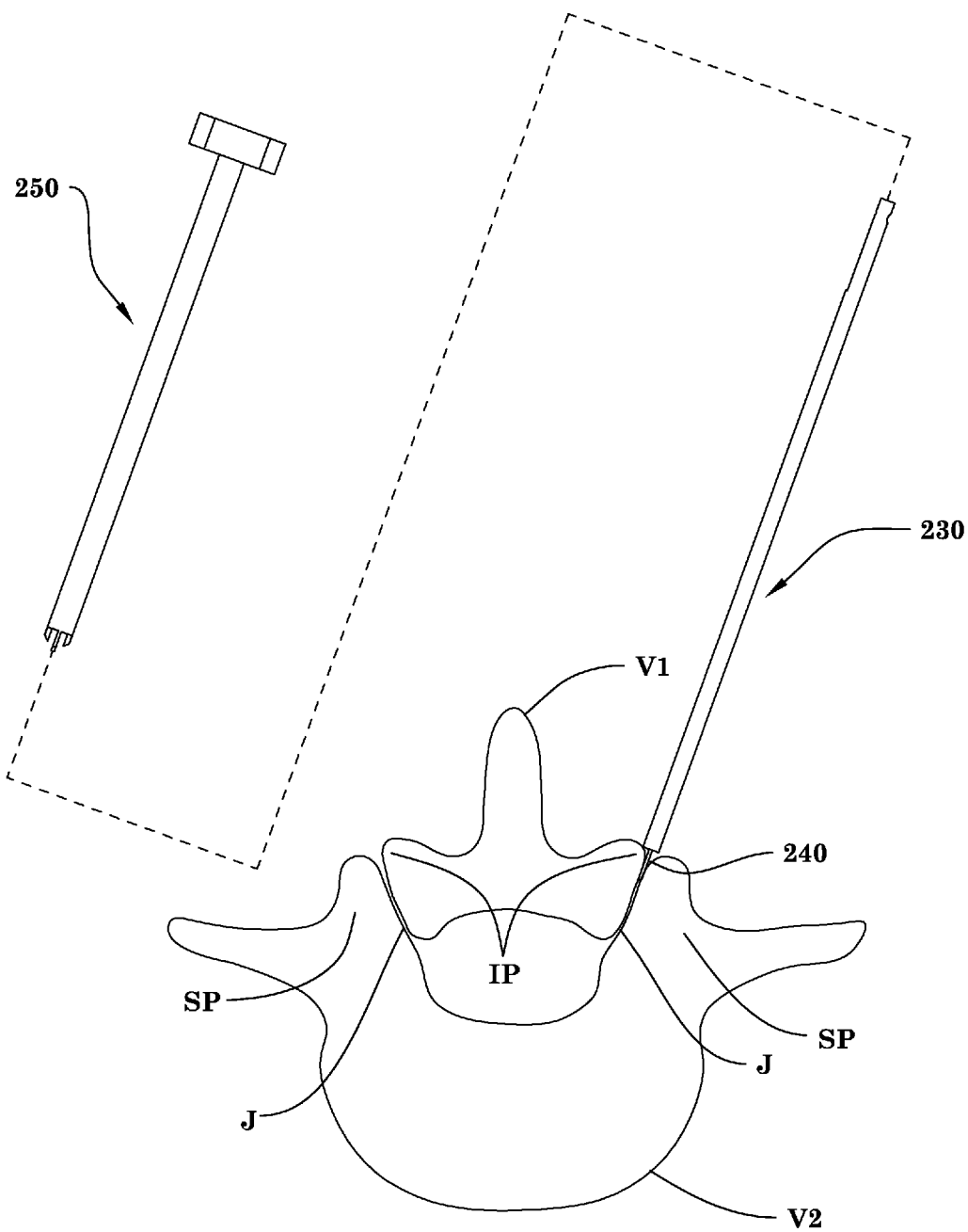
FIGS. 36-38 illustrate various steps of a surgical procedure for implanting the implant illustrated in FIGS. 23-25 in a facet joint in a minimally invasive manner.
Figure 37:
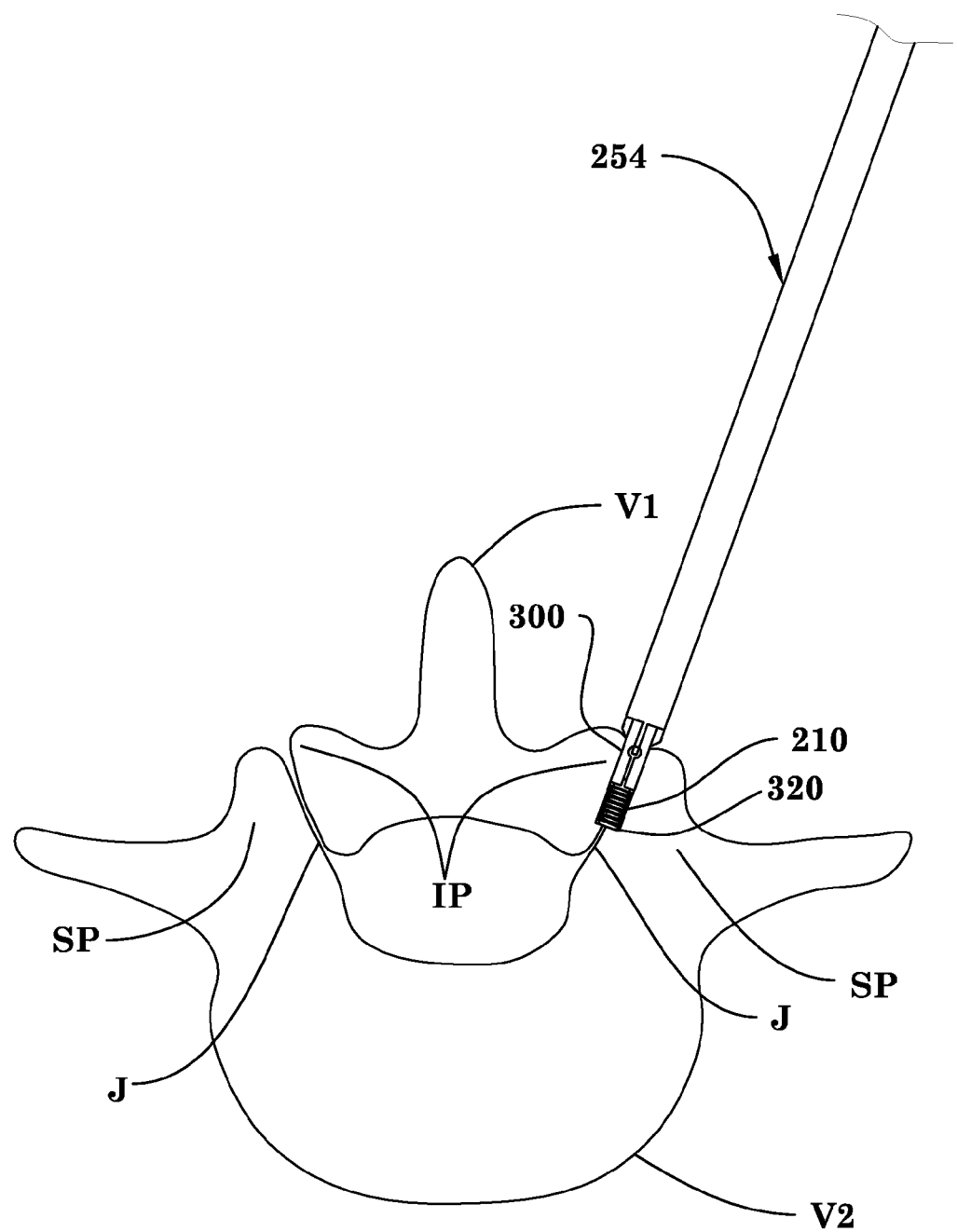
Figure 38:
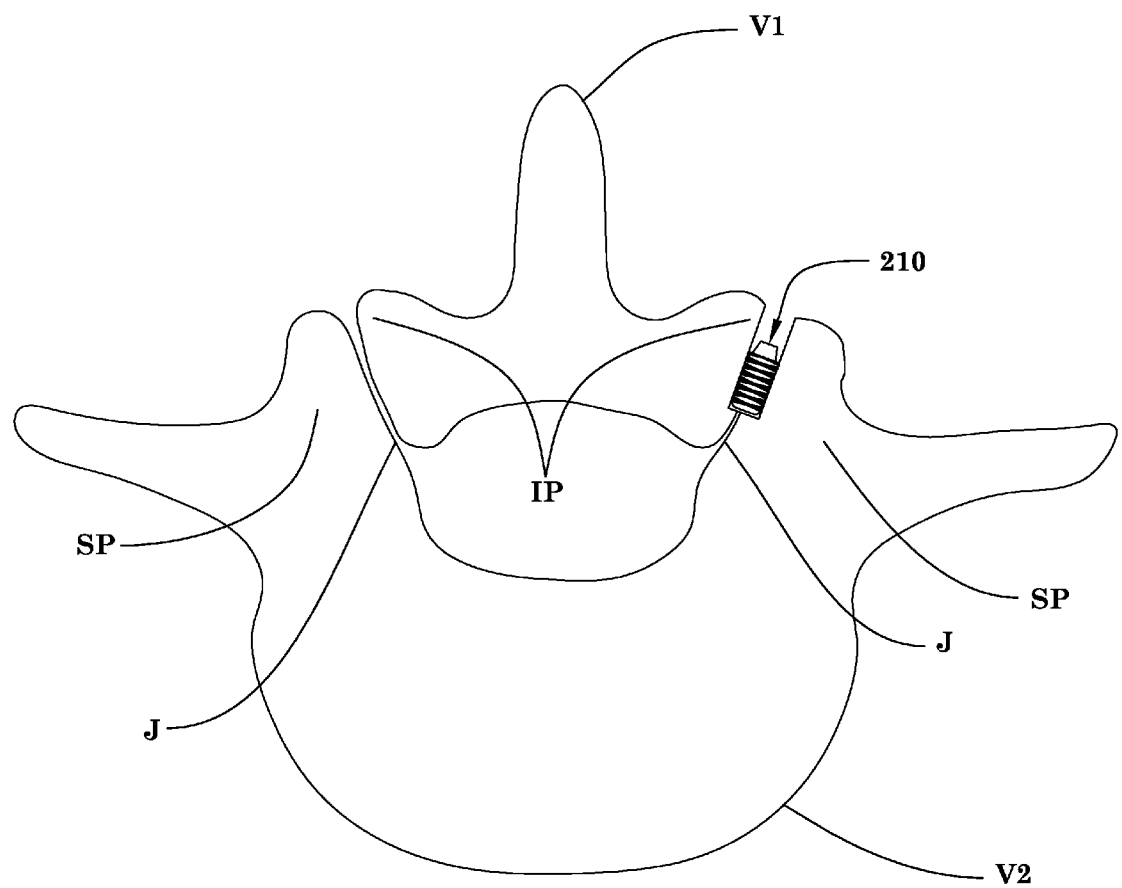

As indicated above, one particular application of the implant 210, the guide instrument 230, the cannula assembly 250, the reamer 280, and the insertion instrument 300 includes a procedure for stabilizing and/or fusing a facet joint J. With further reference to FIGS. 36-38, a method for positioning the implant 210 within a facet joint J between the superior and inferior articular processes SP, IP will be described. However, it should be appreciated that while the implant 210 is described as being used in connection with a surgical procedure performed in relation to the facet joint J, implantation of the implant 210 at other locations along the spinal column and at other anatomical locations are contemplated.

With reference to FIG. 36, the guide instrument 230 is inserted through an incision in the skin and tissue (not shown) and the distal tip 240 is advanced into one of the facet joints J from a generally posterior or postero-lateral approach. In one form, the skin and tissue can be sequentially dilated via a dilation instrument set (not illustrated) inserted over a guidewire and including one or more tissue dilators of increasing size. The tissue dilators are inserted one over another to form a pathway through the skin and tissue to the surgical site. In such procedures, the final dilator is retained in place while the other dilators are removed to leave the working channel of the last dilator open, and the guide instrument 230 is positioned through the final dilator. However, it should be appreciated that insertion and positioning of the guide instrument 230 without guidewires and dilators are also possible and contemplated. As discussed above, in one form, the distal tip 240 of the guide instrument 230 can be used to remove tissue or cartilage from the facet joint J if required. The guide instrument 230 may also be rotated about its axis to distract the superior and inferior articular processes SP, IP if so desired.

Once the distal tip 240 of the guide instrument 230 has been suitably positioned in the facet joint J, the cannula assembly 250 can be positioned thereover until the oppositely positioned prongs 260, 262 of the guide tube 254 are inserted into the facet joint J. Additionally, the oppositely positioned spikes 268, 270 can be engaged with the superior and inferior articular processes SP, IP to anchor the cannula assembly 250 relative to the facet joint J if desired. After the cannula assembly 250 has been suitably positioned relative to the facet joint J, the guide instrument 230 can be proximally withdrawn from the passageway 259, and the reamer 280 can be inserted through the passageway 259 until the fluted cutting portion 288 of the reamer 280 contacts the superior and inferior articular processes SP, IP on opposite sides of the facet joint J. The reamer 280 may then be rotated relative to the cannula assembly 250 in order to remove a portion of bone from each of the superior and inferior articular processes SP, IP so as to define a cavity 320 between the superior and inferior articular processes SP, IP at or near the facet joint J. While not illustrated, it should be appreciated that in another form, the cannula assembly 250 may be rotated in order to distract the superior and inferior articular processes SP, IP before the cavity 320 is formed. In yet another form, the cannula assembly 250 may be rotated in order to distract the superior and inferior articular processes SP, IP after the cavity 320 is formed but before implantation of the implant 210. However, in still other forms, distraction of the superior and inferior articular processes SP, IP with the cannula assembly 250 may not be necessary or desired.

The reamer 280 can be removed from the cannula assembly 250 following the formation of the cavity 320. As illustrated in FIG. 37, the implant 210 may then be engaged with the receptacle 316 of the insertion instrument 300 and advanced distally through the passageway 259 of the cannula assembly 250 and into the cavity 320. While not previously discussed, it should be appreciated that the cavity 320 and the implant 210 can be sized relative to one another such that a friction or press fit is formed between the implant 210 and the cavity 320 in order to retain the implant 210 within the facet joint J, although other variations in the relative size of the implant 210 and the cavity 320 are possible and contemplated. Once the implant 210 has been properly positioned within the cavity 320, the insertion instrument 300 is proximally withdrawn from the cannula assembly 250 in order to release the implant 210 from the receptacle 316. As illustrated in FIG. 38, the cannula assembly 250 is removed form the facet joint J, thereby leaving only the implant 210 at the facet joint J.

Once implanted in the facet joint J between the superior and inferior articular processes SP, IP, the grooves 222, 224 of the implant 210 engage with the superior and inferior articular processes SP, IP to resist expulsion of the implant 10 from the facet joint J. Additionally, while not illustrated in FIGS. 36-38, it is contemplated that the position of the implant 210 may be fixed relative to the superior and inferior articular processes SP, IP by a fastener engaged to one or both of the superior and articular processes SP, IP. Non-limiting examples of fasteners that may be used to secure the implant 210 within the cavity 320 include a pin, a nail, a screw, a staple, or a wedge, just to name a few possibilities. In one particular form, it is contemplated that the bone anchor assembly 90 described above could be used in connection with the implant 210. In one aspect of this form, the implant 210 may be provided with a pre-drilled hole which may be aligned with a hole drilled for the bone screw 92 in order to allow the bone screw 92 to extend through the implant 210. However, in other forms, the bone screw 92 does not extend through the implant 210 and the bone anchor assembly 90 is only used to apply a clamping force to the implant 210 via the superior and inferior articular processes SP, IP.

Alternative configurations and uses of the instruments, devices, systems, techniques and methods described herein are also contemplated. For example, in one form, an implant 10, 210 could be positioned in both of the facet joints J of the spinal motion segment 2 and/or at one or more other vertebral levels of the spinal column in order to perform a surgical procedure across multiple levels of the spinal column. Additionally, implantation of the implants 10, 210 at one or both of the facet joints J of a spinal motion segment could be implemented with other surgical procedures including, for example, fusion of the adjacent vertebrae of the spinal motion segment across the disc space. Furthermore, the use of bone growth promoting materials such as bone chips, bone morphogenetic protein (BMP), LIM mineralization proteins (LMPs), transforming growth factors, such as transforming growth factor-β (BGF-β) insulin-like growth factors, platelet-derived growth factors, fibroblast growth factors, or other similar growth factors that have some beneficial effect, in the facet joint J with either of the implants 10, 210 is also contemplated.

Additionally, the instruments, devices, systems, techniques and methods described herein may also be used in surgical procedures involving animals, or in demonstrations for training, education, marketing, sales and/or advertising purposes. Furthermore, the instruments, devices, systems, techniques and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words/phrases such as "a", "an", "at least one", and/or "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A method for stabilizing a facet joint of the spinal column, comprising:
    inserting a distal end of a guide instrument between adjacent bones forming the facet joint;
    providing a cannula including an elongate body extending between a proximal end and a distal end; distally advancing said cannula over said guide instrument;
    inserting a reamer through said cannula and removing at least a portion of each of the adjacent bones to form a cavity for receiving an implant formed of cancellous bone in the facet joint between the adjacent bones, said implant extending between a proximal end and a distal end and including a support body and a reduced diameter instrument engagement portion extending proximally from a proximally facing end wall of said support body;
    engaging said implant with an insertion instrument and inserting said implant through said cannula into said cavity;
    boring a hole extending transversely to said cavity through a first one of the adjacent bones and at least partially into a second one of the adjacent bones; and
    positioning a bone anchor in said hole and engaging said bone anchor with said first and second ones of the adjacent bones by forcing said first and second ones of the adjacent bones toward one another and clamping said implant between the adjacent bones by fracturing said implant into a plurality of fragments.

2. The method of claim 1, wherein said distal end of said cannula includes a pair of oppositely positioned prongs and distally advancing said cannula includes positioning at least a portion of said prongs in the facet joint between the adjacent bones.

3. The method of claim 2, wherein said distal end of said cannula further includes a pair of oppositely positioned engagement spikes offset from said pair of oppositely positioned prongs, and distally advancing said cannula further includes engaging said spikes with an outer surface of each of the adjacent bones.

4. The method of claim 1, wherein said distal end of said guide instrument includes a pair of oppositely facing surfaces extending distally from a distally facing end wall, said surfaces each extending between oppositely positioned lateral edges and including a width between said lateral edges that is greater than a height between said surfaces.

5. The method of claim 1, which further includes distracting said adjacent bones by at least one of rotating said cannula and rotating said guide instrument.

6. The method of claim 1, wherein inserting said implant includes engaging one or more bone engaging features formed in said support body of said implant with the adjacent bones forming the facet joint.

7. The method of claim 6, wherein said bone engaging features include a pair of oppositely wound grooves extending along said support body.

8. The method of claim 6, wherein said instrument engagement portion tapers from said end wall to said proximal end of said implant.

9. The method of claim 8, wherein said support body tapers from said end wall to said distal end of said implant.

10. The method of claim 8, wherein said insertion instrument includes an internal receptacle configured to receive said instrument engagement portion of said implant and inserting said implant through said cannula into said cavity includes:
    positioning said instrument engagement portion of said implant into said internal receptacle;
    distally advancing said insertion instrument through said cannula until said implant is positioned in said cavity; and
    proximally withdrawing said insertion instrument through said cannula to disengage said implant from said insertion instrument.

11. The method of claim 10, wherein said internal receptacle is positioned between opposite portions of a bifurcated distal end of said insertion instrument, said portions being resiliently deflectable to receive and clamp against said tool engagement portion of said implant to releasably couple said implant with said insertion instrument.

12. A method for stabilization of a facet joint of the spinal column, comprising:
    forming a cavity between adjacent bones defining the facet joint for receiving an implant in the facet joint;

inserting said implant formed of cancellous bone into said cavity;

boring a hole extending transversely to said cavity through a first one of the adjacent bones and at least partially into a second one of the adjacent bones; and positioning a bone anchor in said hole and engaging said bone anchor with said first and second ones of the adjacent bones by forcing said first and second ones of the adjacent bones toward one another and clamping said implant between the adjacent bones by fracturing said implant into a plurality of fragments.

13. The method of claim 12, which further includes boring said hole through a portion of said implant and positioning a portion of said bone anchor through said implant.

14. The method of claim 12, wherein:

said bone anchor includes a threaded distal portion, a threaded proximal portion spaced apart from said threaded distal portion, and a clamping member engageable with said threaded proximal portion; and engaging said bone anchor includes inserting said threaded distal portion through said first one of the adjacent bones and into engagement with said second one of the adjacent bones and advancing said clamping member toward said distal threaded portion and into engagement with an external surface of said first one of the adjacent bones.

15. The method of claim 12, which further includes:

providing a cannula extending between a proximal end including an externally threaded portion and a distal end;

providing a reamer extending between a proximal end including an internally threaded portion and a fluted distal end;

positioning said reamer through said cannula such that said fluted distal end extends distally from said distal end of said cannula and engaging said externally threaded portion with said internally threaded portion to releasably couple said cannula and said reamer; and inserting the coupled reamer and cannula over a guidewire to a location adjacent the facet joint.

16. The method of claim 15, wherein forming said cavity between the adjacent bones defining the facet joint includes rotating the coupled reamer and cannula.

17. The method of claim 16, which further includes removing said reamer from said cannula with said distal end of said cannula positioned adjacent said cavity following completion of said cavity.

18. A method for stabilization of a facet joint of the spinal column, comprising:

providing a cannula extending between a proximal end including an externally threaded portion and a distal end;

providing a reamer extending between a proximal end including an internally threaded portion and a fluted distal end;

positioning said reamer through said cannula such that said fluted distal end extends distally from said distal end of said cannula and engaging said externally threaded portion with said internally threaded portion to releasably couple said cannula and said reamer; and inserting the coupled reamer and cannula over a guidewire to a location adjacent the facet joint;

forming a cavity between adjacent bones defining the facet joint for receiving an implant in the facet joint by rotating the coupled reamer and cannula;

inserting said implant into said cavity;

boring a hole extending transversely to said cavity through a first one of the adjacent bones and at least partially into a second one of the adjacent bones; and positioning a bone anchor in said hole and engaging said bone anchor with said first and second ones of the adjacent bones.

19. The method of claim 18, which further includes removing said reamer from said cannula with said distal end of said cannula positioned adjacent said cavity following completion of said cavity.

20. The method of claim 18, wherein said implant is formed of cancellous bone.

21. The method of claim 18, which further includes boring said hole through a portion of said implant and positioning a portion of said bone anchor through said implant.

* * * * *